(12) United States Patent
Young et al.

(10) Patent No.: US 6,703,359 B1
(45) Date of Patent: Mar. 9, 2004

(54) INOTROPIC AND DIURETIC EFFECTS OF EXENDIN AND GLP-1

(75) Inventors: Andrew A. Young, San Diego, CA (US); Will Vine, Poway, CA (US); Nigel R. A. Beeley, Solana Beach, CA (US); Kathryn Prickett, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/622,105

(22) PCT Filed: Feb. 5, 1999

(86) PCT No.: PCT/US99/02554

§ 371 (c)(1),
(2), (4) Date: Sep. 22, 2000

(87) PCT Pub. No.: WO99/40788

PCT Pub. Date: Aug. 19, 1999

Related U.S. Application Data

(60) Provisional application No. 60/075,122, filed on Feb. 13, 1998.

(51) Int. Cl.$^7$ ............................................... A01N 37/18
(52) U.S. Cl. ........................... 514/2; 514/866; 530/324
(58) Field of Search ...................... 514/2, 866; 530/324

(56) References Cited

U.S. PATENT DOCUMENTS

| | | | |
|---|---|---|---|
| 5,424,286 A | * | 6/1995 | Eng |
| 5,512,549 A | | 4/1996 | Chen et al. |
| 5,545,618 A | | 8/1996 | Buckley et al. |
| 5,574,008 A | | 11/1996 | Johnson et al. |
| 5,846,937 A | * | 12/1998 | Drucker |

FOREIGN PATENT DOCUMENTS

| | | |
|---|---|---|
| WO | WO98 05351 A | 2/1998 |
| WO | WO99 07404 A | 12/1999 |

OTHER PUBLICATIONS

Edwards, "Cardiovascular and Pancreatic Endocrine Responses to GLP–1–(7–36) Amide in the Conscious Calf." *Exp. Physiol.*, 82(4):709–16 (1997).
Barragan, J.M., et al, "Interactions of cxendin–(9–39) with the effects of glucagon–like peptide–1(7–36) amide and of exendin–4 on arterial blood pressure and heart rate in rats," *Regulatory Peptides* 67:63–68 (1996).
Bhavsar, et al, "Inhibition of gastric emptying and of food intake appear to be independently controlled in rodents," *Soc. Neurosci. Abstr.* 21:460 (188.8)(1995).
D'Alessio et al. "Elimination of the Action of glucagon–like Peptide 1 Causes an Impairment of glucose tolerance after Nutrient Ingestion by Healthy Baboons," *J. Clin. Invest*, 97:133–38, 1996.
Eissele et al. "Rat Gastric somatostatin and Gastrin Release: Interactions of Exendin–4 and Truncated Glucagon–Like Peptide–1 (GLP–1) Amide," *Life Sci.*, 55:629–34, 1994.
Eng et al. "Isolation and Characterization of Exendin–4, an Exendin–3 Analogue, from *Heloderma suspectum* Venom", *J. Biol. Chem.*, 267:7402–05, 1992.
Eng et al. "Purification and Structure of Exendin–3, a New Pancreatic Secretagogue Isolated from *Heloderma horridum* Venom," *J. Biol. Chem.*, 265:20259–62, 1990.
Fehmann et al. "Stable Expression of the Rat GLP–I Receptor in CHO Cells: Activation and Binding Characteristics Utilizing GLP–I(7–36)–Amide, Oxyntomodulin, Exendin–4, and Exendin(9–39)," *Peptides* 15 (3): 453–6, 1994.
Ferguson et al. "Cell–Surface Anchoring of Proteins Via Glycosylphosphatidylinositol Structures", *Annu. Rev. Biochem* 57:285–320, 1988.
Goke et al. "Exendin–4 Is a High Potency Agonist and Truncated Exendin–(9–39)–amide an Antagonist at the Glucagon–like Peptide 1–(7–36)–amide Receptor of Insulin–secreting –Cells", *J. Biol. Chem*, 268:19650–55, 1993.
Knudsen, L.B., et al, "Potent Derivatives of Glucagon–like Peptide–1 with Pharmacokinetic Properties Suitable for Once Daily Administration," *J. Med. Chem* 43:1664–1669 (2000).
Kolligs et al. "Reduction of the Incretin effect in Rats by the Glucagon–Like Peptide 1 Receptor antagonist Exendin(9–39) Amide", *Diabetes*, 44:16–19, 1995.
Malhotra et al. "Exendin–4, a new peptide from *Heloderma suspectum* venom, potentiates cholecystokinin–induced amylase release from rat pancreatic acini", *Regulatory Peptides*, 41:149–56, 1992.
Montrose–Rafizadeh et al. "Structure–function Analysis of Exendin–4 /GLP–1 Analogs", *Diabetes*, 45(Suppl 2):152A, 1996.
O'Halloran et al. "Glucagon–like peptide–1 (7–36)–NH$_2$: a physiological inhibitor of gastric acid secretion in man," *J Endocrinol* 126 (1): 169–73, 1990.

(List continued on next page.)

*Primary Examiner*—Leon B. Lankford, Jr.
(74) *Attorney, Agent, or Firm*—Arnold & Porter

(57) ABSTRACT

Methods for increasing urine flow are disclosed, comprising administration of an effective amount of GLP-1, an exendin, or an exendin or GLP-1 agonist. Methods for increasing urinary sodium excretion and decreasing urinary potassium concentration are also disclosed. The methods are useful for treating conditions or disorders associated with toxic hypervolemia, such as renal failure, congestive heart failure, nephrotic syndrome, cirrhosis, pulmonary edema, and hypertension. The present invention also relates to methods for inducing an inotropic response comprising administration of an effective amount of GLP-1, an exendin, or an exendin or GLP-1 agonist. These methods are useful for treating conditions or disorders that can be alleviated by an increase in cardiac contractility such as congestive heart failure. Pharmaceutical compositions for use in the methods of the invention are also disclosed.

42 Claims, 10 Drawing Sheets

OTHER PUBLICATIONS

Ørskov et al. "Biological Effects and Metabolic Rates of Glucagonlike Peptide–1 7–36 Amide and glucagonlike Peptide–1 7–37 in Healthy Subjects Are Indistinguishable", *Diabetes*, 42:658–61, 1993.

Raufman et al. "Truncated Glucagon–like Peptide–1 Interacts with Exendin Receptors in Dispersed Acini from Guinea Pig Pancreas", *J. Biol. Chem*, 267:21432–37, 1992.

Raufman et al. "Exendin–3, a Novel Peptide from *Heloderma horridum* Venom, Interacts with Vasoactive Intestinal Peptide Receptors and a Newly Described Receptor on dispersed Acini from Guinea Pig Pancreas," *J. Biol. Chem.* 266:2897–902, 1991.

Schepp et al. "Exendin–4 and exendin–(9–39)$NH_2$: agonist and antagonist, respectively, at the rat parietal cell receptor for glucagon–like peptide–1–(7–36)$NH_2$," *Eur. J. Pharm* 269:183–91, 1994.

Schjoldager et al. "GLP–1 (Glucagon–like Peptide 1) and Truncated GLP–1, Fragments of Human Proglucagon, Inhibit Gastric Acid Secretion in Humans," *Dig Dis Sci* 34 (5): 703–8, 1989.

Singh et al. "Use of $^{125}I$–[$Y^{39}$]exendin–4 to characterize exendin receptros on dispersed pancreatic acini and gastric chief cells from guinea pig," *Regul. Pept.* 53:47–59, 1994.

Tang–Christensen, M., et al, "Central administration of GLP–1–(7–36) amide inhibits food and water intake in rats," *Am J Physiol* 271:R848–56 (1996).

Thorens et al. "Cloning and Functional Expression of the Human Islet GLP–1 Receptor," *Diabetes* 42 (11): 1678–82, 1993.

Thorens, "Expression cloning of the pancreatic cell receptor for the gluco–incretin hormone glucagon–like peptide 1," *Proc. Natl. Acad. Sci. USA* 89:8641–45 1992.

Turton, et al, "A role for glucagon–like peptide–1 in the central regulation of feeding," *Nature* 379:69–72 (1996).

Wang et al. "Glucagon–like Peptide–1 Is a Physiological Incretin in Rat," *J. Clin. Invest*, 95:417–21, 1995.

Wettergren et al. "Truncated GLP–1 (Proglucagon 78–107–Amide) Inhibits Gastric and Pancreatic Functions in Man," *Dig Dis Sci* 38 (4): 665–73, 1993.

Willms et al. "Gastric Emptying, Glucose Responses, and Insulin Secretion after a Liquid Tes Mcl: Effects of Exogenous Glucagon–Like Peptide–1 (GLP–1)–(7–36) Amide in Type 2 (Noninsulin–Dependent) Diabetic Patients," *J. Clin. Endocrinol. Metab.* 81(1):327–32 1996.

Young, A.A., et al, "Preclinical Pharmacology of Pramlintide in the Rat: Comparisons with Human and Rat Amylin," *Drug Development Research* 37: 231–248 (1996).

* cited by examiner

SEQUENCE LISTING

```
<160> NUMBER OF SEQ ID NOS: 65

<210> SEQ ID NO 1
<211> LENGTH: 39
<212> TYPE: PRT
<213> ORGANISM: Heloderma horridum
<220> FEATURE:
<223> OTHER INFORMATION: Exendin-3

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Ser
        35

<210> SEQ ID NO 2
<211> LENGTH: 39
<212> TYPE: PRT
<213> ORGANISM: Heloderma suspectum
```

```
<220> FEATURE:
<223> OTHER INFORMATION: Exendin-4

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 3
<211> LENGTH: 30
<212> TYPE: PRT
<213> ORGANISM: Homo sapiens
<220> FEATURE:
<223> OTHER INFORMATION: GLP-1

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
                20                  25                  30

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Exendin or
      exendin agonist
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Asp or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
```

```
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)...(17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine, tert-butylglycine
      or Met
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp, Phe, Tyr or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine N-alkylpentylglycine or N-alkylalanine
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine N-alkylpentylglycine or N-alkylalanine
<220> FEATURE:
<221> NAME/KEY: MOD_RES
<222> LOCATION: (39)
<223> OTHER INFORMATION: Ser, Thr, Tyr, Pro, homoproline, 3Hyp, 4Hyp,
      thioproline, N-alkylglycine, N-alkylpentylglycine or
      N-alkylalanine
<220> FEATURE:
<223> OTHER INFORMATION: provided no more than three of Xaa3, Xaa5,
      Xaa6, Xaa8, Xaa10, Xaa11, Xaa12, Xaa13, Xaa14, Xaa15, Xaa16,
      Xaa17, Xaa19, Xaa20, Xaa21, Xaa24, Xaa25, Xaa26, Xaa27 or Xaa28
      are Ala; and the compound is not exendin-3 or exendin-4
<220> FEATURE:
<223> OTHER INFORMATION: this peptide may encompass 28-39 residues,
``` wherein residues 1-28 are constant and residues 29-39 may vary
        in length according to the specification

<400> SEQUENCE: 4

Xaa Xaa Xaa Gly Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term may be amidated

<400> SEQUENCE: 5

His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn Gly Gly
            20                  25                  30

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 6

His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 7

His Gly Glu Gly Thr Phe Thr Ser Asp Leu Ser Lys Gln Leu Glu Glu
 1               5                   10                  15

Glu Ala Val Arg Leu Phe Ile Glu Phe Leu Lys Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist

```
<220> FEATURE:
<223> OTHER INFORMATION: C-term amidated

<400> SEQUENCE: 8

His Ala Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 9

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 10

His Gly Glu Gly Thr Ala Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 11

His Gly Glu Gly Thr Phe Thr Ala Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated
```

```
<400> SEQUENCE: 12

His Gly Glu Gly Thr Phe Thr Ser Asp Ala Ser Lys Gln Leu Glu Glu
  1               5                  10                  15

Glu Ala Val Arg Leu Phe Ile Glu Phe Leu Lys Asn
             20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 13

His Gly Glu Gly Thr Phe Thr Ser Asp Leu Ala Lys Gln Leu Glu Glu
  1               5                  10                  15

Glu Ala Val Arg Leu Phe Ile Glu Phe Leu Lys Asn
             20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 14

His Gly Glu Gly Thr Phe Thr Ser Asp Leu Ser Lys Ala Leu Glu Glu
  1               5                  10                  15

Glu Ala Val Arg Leu Phe Ile Glu Phe Leu Lys Asn
             20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 15

His Gly Glu Gly Thr Phe Thr Ser Asp Leu Ser Lys Gln Ala Glu Glu
  1               5                  10                  15

Glu Ala Val Arg Leu Phe Ile Glu Phe Leu Lys Asn
             20                  25

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 16

His Gly Glu Gly Thr Phe Thr Ser Asp Leu Ser Lys Gln Ala Glu Glu
```

```
                1               5                  10                 15
Glu Ala Val Arg Leu Phe Ile Glu Phe Leu Lys Asn
                    20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 17

His Gly Glu Gly Thr Phe Thr Ser Asp Leu Ser Lys Gln Leu Ala Glu
  1               5                  10                 15
Glu Ala Val Arg Leu Phe Ile Glu Phe Leu Lys Asn
                    20                  25

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 18

His Gly Glu Gly Thr Phe Thr Ser Asp Leu Ser Lys Gln Leu Glu Ala
  1               5                  10                 15
Glu Ala Val Arg Leu Phe Ile Glu Phe Leu Lys Asn
                    20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 19

His Gly Glu Gly Thr Phe Thr Ser Asp Leu Ser Lys Gln Leu Glu Glu
  1               5                  10                 15
Ala Ala Val Arg Leu Phe Ile Glu Phe Leu Lys Asn
                    20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 20

His Gly Glu Gly Thr Phe Thr Ser Asp Leu Ser Lys Gln Leu Glu Glu
  1               5                  10                 15
Glu Ala Ala Arg Leu Phe Ile Glu Phe Leu Lys Asn
```

```
            20                  25

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 21

His Gly Glu Gly Thr Phe Thr Ser Asp Leu Ser Lys Gln Leu Glu Glu
  1               5                  10                  15

Glu Ala Val Ala Leu Phe Ile Glu Phe Leu Lys Asn
            20                  25

<210> SEQ ID NO 22
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 22

His Gly Glu Gly Thr Phe Thr Ser Asp Leu Ser Lys Gln Leu Glu Glu
  1               5                  10                  15

Glu Ala Val Arg Ala Phe Ile Glu Phe Leu Lys Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 23

His Gly Glu Gly Thr Phe Thr Ser Asp Leu Ser Lys Gln Leu Glu Glu
  1               5                  10                  15

Glu Ala Val Arg Leu Phe Ile Ala Phe Leu Lys Asn
            20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 24

His Gly Glu Gly Thr Phe Thr Ser Asp Leu Ser Lys Gln Leu Glu Glu
  1               5                  10                  15

Glu Ala Val Arg Leu Phe Ile Glu Ala Leu Lys Asn
            20                  25
```

```
<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 25

His Gly Glu Gly Thr Phe Thr Ser Asp Leu Ser Lys Gln Leu Glu Glu
 1               5                  10                  15

Glu Ala Val Arg Leu Phe Ile Glu Phe Ala Lys Asn
             20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 26

His Gly Glu Gly Thr Phe Thr Ser Asp Leu Ser Lys Gln Leu Glu Glu
 1               5                  10                  15

Glu Ala Val Arg Leu Phe Ile Glu Phe Leu Ala Asn
             20                  25

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 27

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Ala
             20                  25

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 28

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro
         35
```

```
<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 29

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Exendin or
      GLP-1 agonist

<400> SEQUENCE: 30

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 31

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 32

His Gly Glu Gly Thr Phe Thr Ser Asp Leu Ser Lys Gln Met Glu Glu
 1               5                  10                  15
```

Glu Ala Val Arg Leu Phe Ile Glu Trp Leu Lys Asn Gly Gly Pro Ser
            20                  25                  30

Ser Gly Ala Pro
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 33

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 34
<211> LENGTH: 35
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 34

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 35

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
            20                  25                  30

Ser Gly Ala
        35

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Exendin or

```
         GLP-1 agonist
<220> FEATURE:
<223> OTHER INFORMATION: C-term amidated

<400> SEQUENCE: 36

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 37

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly

<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 38

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 39

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser

<210> SEQ ID NO 40
```

```
<211> LENGTH: 32
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 40

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 41

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Description of Artificial Sequence: Exendin or
      GLP-1 agonist

<400> SEQUENCE: 42

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro
             20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 43

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro
             20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Exendin or
```

```
        GLP-1 agonist

<400> SEQUENCE: 44

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly
            20                  25                  30

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Exendin or
      GLP-1 agonist

<400> SEQUENCE: 45

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly
            20                  25

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 46

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly
            20                  25

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (31)
<223> OTHER INFORMATION: tPro
<220> FEATURE:
<221> NAME/KEY: MOD_RES
<222> LOCATION: (36)..(38)
<223> OTHER INFORMATION: tPro
<220> FEATURE:
<223> OTHER INFORMATION: C-term amidated

<400> SEQUENCE: 47

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa
        35

<210> SEQ ID NO 48
<211> LENGTH: 38
```

<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (36)..(38)
<223> OTHER INFORMATION: tPro
<220> FEATURE:
<223> OTHER INFORMATION: C-term amidated

<400> SEQUENCE: 48

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Xaa Xaa Xaa
         35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (31)
<223> OTHER INFORMATION: NMeala
<220> FEATURE:
<223> OTHER INFORMATION: C-term amidated

<400> SEQUENCE: 49

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Pro Pro
         35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (31)
<223> OTHER INFORMATION: NMeala
<220> FEATURE:
<221> NAME/KEY: MOD_RES
<222> LOCATION: (36)..(37)
<223> OTHER INFORMATION: NMeala
<220> FEATURE:
<223> OTHER INFORMATION: C-term amidated

<400> SEQUENCE: 50

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Xaa Ser
             20                  25                  30

Ser Gly Ala Xaa Xaa
         35

```
<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (31)
<223> OTHER INFORMATION: hPro
<220> FEATURE:
<221> NAME/KEY: MOD_RES
<222> LOCATION: (36)..(37)
<223> OTHER INFORMATION: hPro
<220> FEATURE:
<223> OTHER INFORMATION: C-term amidated

<400> SEQUENCE: 51

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Xaa Xaa
         35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (31)
<223> OTHER INFORMATION: hPro
<220> FEATURE:
<221> NAME/KEY: MOD_RES
<222> LOCATION: (36)
<223> OTHER INFORMATION: hPro
<220> FEATURE:
<223> OTHER INFORMATION: C-term amidated

<400> SEQUENCE: 52

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Xaa
         35

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 53

Arg Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30
```

```
Ser Gly Ala
        35

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 54

His Gly Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (6)
<223> OTHER INFORMATION: Naphthylala
<220> FEATURE:
<223> OTHER INFORMATION: C-term amidated

<400> SEQUENCE: 55

His Gly Glu Gly Thr Xaa Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 56

His Gly Glu Gly Thr Phe Ser Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 57

His Gly Glu Gly Thr Phe Ser Thr Asp Leu Ser Lys Gln Met Glu Glu
 1               5                  10                  15
```

Glu Ala Val Arg Leu Phe Ile Glu Trp Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 58

His Gly Glu Gly Thr Phe Thr Ser Glu Leu Ser Lys Gln Met Ala Glu
 1               5                  10                  15

Glu Ala Val Arg Leu Phe Ile Glu Trp Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (10)
<223> OTHER INFORMATION: pentylgly
<220> FEATURE:
<223> OTHER INFORMATION: C-term amidated

<400> SEQUENCE: 59

His Gly Glu Gly Thr Phe Thr Ser Asp Xaa Ser Lys Gln Leu Glu Glu
 1               5                  10                  15

Glu Ala Val Arg Leu Phe Ile Glu Phe Leu Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (22)
<223> OTHER INFORMATION: Naphthylala
<220> FEATURE:
<223> OTHER INFORMATION: C-term amidated

<400> SEQUENCE: 60

His Gly Glu Gly Thr Phe Thr Ser Asp Leu Ser Lys Gln Leu Glu Glu
 1               5                  10                  15

Glu Ala Val Arg Leu Xaa Ile Glu Phe Leu Lys Asn
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES
<222> LOCATION: (23)
<223> OTHER INFORMATION: tButylgly
<220> FEATURE:
<223> OTHER INFORMATION: C-term amidated

<400> SEQUENCE: 61

His Gly Glu Gly Thr Phe Thr Ser Asp Leu Ser Lys Gln Met Glu Glu
  1               5                  10                  15

Glu Ala Val Arg Leu Phe Xaa Glu Trp Leu Lys Asn
             20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 62

His Gly Glu Gly Thr Phe Thr Ser Asp Leu Ser Lys Gln Leu Glu Glu
  1               5                  10                  15

Glu Ala Val Arg Leu Phe Ile Asp Phe Leu Lys Asn
             20                  25

<210> SEQ ID NO 63
<211> LENGTH: 33
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 63

His Gly Glu Gly Thr Phe Thr Ser Asp Ala Ser Lys Gln Leu Glu Glu
  1               5                  10                  15
Glu Ala Val Arg Leu Phe Ile Glu Phe Leu Lys Asn Gly Gly Pro Ser
             20                  25                  30
Ser

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<223> OTHER INFORMATION: C-term amidated

<400> SEQUENCE: 64

His Gly Glu Gly Thr Phe Thr Ser Asp Ala Ser Lys Gln Met Glu Glu
  1               5                  10                  15
Glu Ala Val Arg Leu Phe Ile Glu Trp Leu Lys Asn Gly
             20                  25

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Exendin or
      GLP-1 agonist
<220> FEATURE:
<221> NAME/KEY: MOD_RES -continued

```
<222> LOCATION: (31)
<223> OTHER INFORMATION: hPro
<220> FEATURE:
<221> NAME/KEY: MOD_RES
<222> LOCATION: (36)..(37)
<223> OTHER INFORMATION: hPro
<220> FEATURE:
<223> OTHER INFORMATION: C-term amidated

<400> SEQUENCE: 65

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn Gly Gly Xaa Ser
                20                  25                  30

Ser Gly Ala Xaa Xaa
            35
```

INOTROPIC AND DIURETIC EFFECTS OF EXENDIN AND GLP-1

This application claims the benefit of Provisional application Ser. No. 60/075,122, filed Feb. 13, 1998.

FIELD OF THE INVENTION

The present invention relates to methods for increasing urine flow comprising administration of an effective amount of glucagon-like peptide-1[7–36] amide (abbreviated "GLP-[7–36]NH$_2$" or simply "GLP-1"), an exendin, or an exendin or GLP-1 agonist. Methods for increasing urinary sodium excretion and decreasing urinary potassium concentration are also disclosed. The methods are useful for treating conditions or disorders associated with toxic hypervolemia, such as renal failure, congestive heart failure, nephrotic syndrome, cirrhosis, pulmonary edema, and hypertension. Pharmaceutical compositions for use in the methods of the invention are also disclosed.

The present invention also relates to methods for inducing an inotropic response comprising administration of an effective amount of an exendin, GLP-1, or an exendin or GLP-1 agonist. These methods are useful for treating conditions or disorders that can be alleviated by an increase in cardiac contractility, such as congestive heart failure.

The following description summarizes information relevant to the present invention. It is not an admission that any of the information provided herein is prior art to the presently claimed invention, nor that any of the publications specifically or implicitly referenced are prior art to that invention.

GLP-1

Glucagon-like peptide-1[7–36] amide (also referred to as GLP-1[7–36]NH$_2$ or GLP-1) is a product of the proglucagon gene. It is secreted into plasma mainly from the gut and produces a variety of biological effects related to pancreatic and gastrointestinal function. The parent peptide, proglucagon (PG), has numerous cleavage sites that produce other peptide products dependent on the tissue of origin including glucagon (PG[32–62]) and GLP-1[7–36]NH$_2$ (PG[72–107]) in the pancreas, and GLP-1[7–37] (PG[78–108]) and GLP-1[7–36]NH$_2$ (PG[78–107]) in the L cells of the intestine where GLP-1[7–36]NH$_2$ (78–107 PG) is the major product.

GLP-1[7–36]NH$_2$, also known as proglucagon [78–107], or commnonly, just GLP-1," as used herein, has an insulinotropic effect, stimulating insulin secretion from pancreatic –cells; GLP-1 also inhibits glucagon secretion from pancreatic –cells (Orskov, et al., *Diabetes*, 42:658–61, 1993; D'Alessio, et al., *J. Clin. Invest.*, 97:133–38, 1996). GLP-1 is reported to inhibit gastric emptying (Williams B, et al., *J Clin Endocrinol Metab* 81 (1): 327–32, 1996; Wettergren A, et al., *Dig Dis Sci* 38 (4): 665–73, 1993), and gastric acid secretion. (Schjoldager BT, et al., *Dig Dis Sci* 34 (5): 703–8, 1989; O'Halloran DJ, et al., *J Endocrinol* 126 (1): 169–73, 1990; Wettergren A, et al., *Dig Dis Sci* 38 (4): 665–73, 1993). A diuretic, antidypsogenic effect of intracerebroventricular administration of GLP-1 has been reported, however, this report claims that a peripheral, intraperitoneal injection of GLP-1 did not have this effect. (Tand-Christensen et al., *Am. J. Physiol.*, 271:R848–56, 1996). GLP-1[7–37], which has an additional glycine residue at its carboxy terminus, also stimulates insulin secretion in humans (Orskov, et al., *Diabetes*, 42:658–61, 1993). A transmembrane G-protein adenylate-cyclase-coupled receptor believed to be responsible for the insulinotropic effect of GLP-1 has been cloned from a –cell line (Thorens, *Proc. Natl. Acad. Sci.*, USA 89:8641–45, 1992).

Glucagon and glucagon-like peptides have been found to have different cardiovascular effects. Glucagon has been reported to have positive inotropic and chronotropic effects, produce a slight increase in arterial blood pressure in normal individuals, and affect regional blood circulation. GLP-1 has been found to produce a moderate increase in both systolic and diastolic blood pressure, while GLP-2 has no effect on those parameters. GLP-1, administered through the jugular vein, has been reported to induce an increase in systolic and diastolic blood pressure and heart rate. (Reviewed in Barragan, J. M., et al., *Regul. Peptides*, 67:63–68, 1996).

EXENDIN

Exendins are peptides that are found in the venom of the Gila-monster, a lizard endogenous to Arizona, and the Mexican Beaded Lizard. Exendin-3 is present in the venom of *Heloderma horridum*, and exendin-4 is present in the venom of *Heloderma suspectum* (Eng, J., et al., *J. Biol. Chem.*, 265:20259–62, 1990; Eng., J., et al., *J. Biol. Chem.*, 267:7402–05, 1992). The exendins have some sequence similarity to several members of the glucagon-like peptide family, with the highest homology, 53%, being to GLP-1 (Goke, et al., *J. Biol. Chem.*, 268:19650–55, 1993).

Exendin-4 is a potent agonist at GLP-1 receptors on insulin-secreting TC1 cells, at dispersed acinar cells from guinea pig pancreas, and at parietal cells from stomach; the peptide also stimulates somatostatin release and inhibits gastrin release in isolated stomachs (Goke, et al., *J. Biol. Chem.* 268:19650–55, 1993; Schepp, et al., *Eur. J. Pharmacol.*, 69:183–91, 1994; Eissele, et al., *Life Sci.*, 55:629–34, 1994). Exendin-3 and exendin-4 were found to be GLP-1 agonists in stimulating cAMP production in, and amylase release from, pancreatic acinar cells (Malhotra, R., et al., *Relulatory Peptides*, 41:149–56, 1992; Raufman, et al., *J. Biol. Chem.* 267:21432–37, 1992; Singh, et al., *Regul. Pept.* 53:47–59, 1994). The use of the insulinotropic activities of exendin-3 and exendin-4 for the treatment of diabetes mellitus and the prevention of hyperglycemia has been proposed (Eng, U.S. Pat. No. 5,424,286).

Truncated exendin peptides such as exendin[9–39], a carboxyamidated molecule, and fragments 3–39 through 9–39 have been reported to be potent and selective antagonists of GLP-1 (Goke, et al., *J. Biol. Chem.*, 268:19650–55, 1993; Raufman, J. P., et al., *J. Biol. Chem.* 266:2897–902, 1991; Schepp, W., et al., *Eur. J. Pharm.* 269:183–91, 1994; Montrose-Rafizadeh, et al., *Diabetes*, 45(Suppl. 2):152A, 1996). Exendin[9–39] blocks endogenous GLP-1 in vivo, resulting in reduced insulin secretion. Wang, et al., *J. Clin. Invest.*, 95:417–21, 1995; D'Alessio, et al., *J. Clin. Invest.*, 97:133–38, 1996). The receptor apparently responsible for the insulinotropic effect of GLP-1 has been cloned from rat pancreatic islet cells (Thorens, B., *Proc. Natl. Acad. Sci. USA* 89:8641–8645, 1992). Exendins and exendin[9–39] bind to the cloned GLP-1 receptor (rat pancreatic –cell GLP-1 receptor: Fehmann HC, et al., *Peptides* 15 (3): 453–6, 1994; human GLP-1 receptor: Thorens B, et al., *Diabetes* 42 (11): 1678–82, 1993). In cells transfected with the cloned GLP-1 receptor, exendin-4 is an agonist, i.e., it increases cAMP, while exendin[9–39] is an antagonist, i.e., it blocks the stimulatory actions of exendin-4 and GLP-1. Id.

Exendin[9–39] also acts as an antagonist of the full length exendins, inhibiting stimulation of pancreatic acinar cells by exendin-3 and exendin-4 (Raufman, et al., *J. Biol. Chem.* 266:2897–902, 1991; Raufman, et al., *J. Biol. Chem.*, 266:21432–37, 1992). Exendin[9–39] inhibits the stimulation of plasma insulin levels by exendin-4, and inhibits the somatostatin release-stimulating and gastrin release-inhibiting activities of exendin-4 and GLP-1 (Kolligs, F., et al., *Diabetes*, 44:16–19, 1995; Eissele, et al., *Life Sciences*, 55:629–34, 1994). Exendin-4, administered through the jugular vein, has been reported to induce an increase in systolic, diastolic and mean arterial blood pressure, and in heart rate (Barragán, et al., *Repul. Pep.* 67:63–68, 1996).

Exendins have recently been found to inhibit gastric emptying (U.S. patent application Ser. No. 08/694,954, filed Aug. 8, 1996, which enjoys common ownership with the present invention and is hereby incorporated by reference). Exendin[9–39] has been used to investigate the physiological relevance of central GLP-1 in control of food intake (Turton, M. D. et al., *Nature*, 379:69–72, 1996). GLP-1 administered by intracerebroventricular (ICV) injection inhibits food intake in rats. This satiety-inducing effect of GLP-1 delivered by intracerebroventricular injection is reported to be inhibited by ICV injection of exendin[9–39] (Turton, supra). However, it has been reported that GLP-1 does not inhibit food intake in mice when administered by peripheral injection (Turton, M. D., *Nature* 379:69–72, 1996; Bhavsar, S. P., *Soc. Neurosci. Abstr.* 21:460 (188.8), 1995). Administration of exendins and exendin agonists has also recently been found to reduce food intake (U.S. Provisional Patent Application Serial No. 60/034,905, filed Jan. 7, 1997, which enjoys common ownership with the present invention and is hereby incorporated by reference).

DIURETICS

Agents that increase urine flow, or diuretics, are useful for treating conditions or disorders that are associated with toxic hypervolemic states. Such conditions or disorders include renal failure, congestive heart failure, nephrotic syndrome, cirrhosis, pulmonary edema, and hypertension. Diuretics are also employed to treat conditions in pregnancy, such as pre-eclampsia and eclampsia. Further uses of diuretics include their use to reduce volume before some surgical procedures such as ocular surgery and neurosurgery.

One difficulty encountered with many diuretics such as thiazides, loop diuretics, carbonic anhydrase inhibitors, and osmotic diuretics, is that although they may be employed to increase sodium excretion, they also result in an increase of urinary potassium loss. Examples of the effects of potassium loss include muscular weakness, paralysis (including the paralysis of respiratory muscles), electrocardiographic abnormalities, cardiac dysrhythmia, and cardiac arrest.

Another difficulty encountered with some diuretics is their slow rate of action, which is not conducive to their use in an emergency setting.

Thus, there is a need for a method of increasing urine flow that does not deplete potassium concentration in the patient and which has a rapid mode of action. Such methods, and compounds and compositions which are useful therefore, have been invented and are described and claimed herein.

Inotropic Compounds

Compounds that induce inotropic effects (e.g., increase of force of contraction of the heart) have been recognized as being useful for the treatment of, for example, congestive heart failure. Congestive heart failure, which is one of the most common causes of death and disability in industrialized nations, has a mortality rate of about 50% at five years (Goodman and Gilman s The Pharmacological Basis of Therapeutics, 9th Ed. McGraw Hill, N.Y., pp. 809–838).

Inotropic agents currently in clinical use include digitalis, sympathomimetic amines and amrinone (Harrison s Principles of Internal Medicine, 12th Edition, 1991, McGraw Hill, N.Y., pp. 894–899).

Digotoxin, a cardiac glycoside, an ancient but effective therapy for cardiac failure, was initially derived from the foxglove leaf, *Digitalis purpurea* and *Digitalis lanata*. Cardiac glycosides are potent and highly selective inhibitors of the active transport of sodium and potassium ions across cell membranes (Goodman and Gilman, supra). Cardiac glycosides have been reported to increase the velocity of shortening of cardiac muscle, resulting in an improvement in ventricular fumction; this effect has been reported to be due to an increase in the availability during systole of cytosolic $Ca^{2+}$ to interact with contractile proteins in increase the velocity and extent of sarcomere shortening (Goodman and Gilman, supra).

Digotoxin and related cardiac glycosides (e.g. digitoxin) have useful durations of action because their excretion, mainly via the kidneys, results in plasma t of 1.5–5 days. But the therapeutic index of these drugs is very low with mildly toxic:minimally-effective dose ratio being 2:1 and lethal:minimally-effective dose ratio being between 5:1 and 10:1. Urinary potassium loss due to use of thiazide and loop diuretics may seriously enhance the dangers of digitalis intoxication, including susceptibility to cardiac arrhnthmia, and potassium-sparing diuretics are often necessary. Slow elimination of cardiac glycosides can prolong the period of jeopardy during digitalis intoxication, which has been reported to occur in 20% of hospital patients on these drugs. Absorption and onset of action for all cardiac glycosides except ouabain is somewhat prolonged, and this may be a disadvantage in emergency cardiac conditions.

Sympathomimetic amines, which generally include epinephrine, isoproterenol, dopamine and dobutamine, can be useful in an acute setting to stimulate myocardial contractility, but they usually require constant intravenous infusion and continuous intensive monitoring of the patient. They typically lose their effectiveness after 8 hours, apparently due to receptor downregulation.

Amrinone, a noncatecholamine, non-glycoside agent also requires continuous intravenous administration.

This description of available inotropic agents illustrates the need for, and desirability of, therapies that are (1) inotropic, with (2) rapid onset of action, with (3) prolonged duration of action (including a persistent effect, with absence of tachyphylaxis), with (4) low toxicity (a high ratio of toxic to therapeutic dose), with (5) rapid and profound diuretic effect, with (6) a sparing of urinary potassium loss, and with (7) a convenient (non-intravenous) route of administration. We have discovered that exendin and GLP-1 fulfill these criteria.

SUMMARY OF THE INVENTION

The present invention concerns the surprising discovery that exendins, GLP-1, and agonists of these compounds have rapid inotropic and diuretic effects. Although GLP-1 has been reported to not have a diuretic effect when administered peripherally, we have found, surprisingly, that GLP-1 does in fact have a diuretic effect after peripheral administration. This diuretic effect of exendins, GLP-1, and exendin and GLP-1 agonists, is accompanied by an increase in urinary sodium concentration. This diuretic effect is also accompanied by a decrease in urinary potassium concentration which is unanticipated as many diuretics have been found to cause a profound increase in urinary potassium concentration.

The present invention is directed to novel methods for increasing urine flow comprising the administration of an exendin, for example, exendin-3 [SEQ ID NO. 1: His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$], or exendin-4 [SEQ ID NO. 2: His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$], or other compounds which effectively bind to the receptor at which exendin exerts its action on increasing urine flow (exendin agonists). The present invention is also directed to novel methods for increasing urine flow comprising the administration of GLP-1[SEQ ID NO. 3: His Ala Glu Gly Thr Phe Thr Ser Asp Val Ser Ser Tyr Leu Glu Gly Gln Ala Ala Lys Glu Phe Ile Ala Trp Leu Val Lys Gly Arg-NH$_2$], or other compounds which effectively bind to the receptor at which GLP-1 exerts its action on increasing urine flow (GLP-1 agonists).

In a first aspect, the invention features a method of increasing urine flow in an individual comprising administering to the individual a therapeutically effective amount of an exendin or an exendin agonist. In one preferred aspect, said exendin is exendin-3. More preferably, said exendin is exendin-4. By an exendin agonist is meant a compound that mimics the effects of exendin on increasing urine flow, increasing sodium excretion, and/or decreasing urinary potassium concentration, (the potassium concentration in excreted urine) by binding to the receptor or receptors where exendin causes this effect. Certain novel exendin agonist compounds are described in U.S. Provisional Patent Application Serial No. 60/055,404, filed Aug. 8, 1997, which enjoys common ownership with the present invention and is hereby incorporated by this reference. Certain other novel exendin agonist compounds are described in U.S. Provisional Patent Application Serial Nos. 60/066,029 and 60/065,442, both filed Nov. 14, 1997 which enjoy conunon ownership with the present invention and are hereby incorporated by this reference. Preferred exendin agonist compounds include those described in U.S. Provisional Patent Application Serial Nos. 60/055,404 and 60/065,442.

In one preferred aspect the exendin or exendin agonist used in the methods of the present invention is exendin-4. In another preferred aspect, the exendin is exendin-3. In other preferred aspects, the exendin or exendin agonist is a compound of the formula (I) [SEQ ID NO. 4]:

Xaa$_1$ Xaa$_2$ Xaa$_3$ Gly Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$; wherein Xaa$_1$ is His, Arg or Tyr;
Xaa$_2$ is Ser, Gly, Ala or Thr;
Xaa$_3$ is Asp or Glu;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Ala or Lys;
Xaa$_{28}$ is Ala or Asn;
Z$_1$ is —OH,
—NH$_2$,
Gly-Z$_2$,
Gly Gly-Z$_2$,
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$,
Gly Gly Xaa$_{31}$ Ser Ser Gly Ala Xaa$_{36}$ Xaa$_{37}$ Xaa$_{38}$-Z$_2$, or
Gly Gly Xaa31 Ser Ser Gly Ala Xaa$_{36}$ Xaa$_{37}$ Xaa$_{38}$ Xaa$_{39}$-Z2;
wherein Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; Xaa$_{39}$ is Ser, Thr or Tyr; and Z$_2$ is —OH or —NH$_2$; and pharmaceutically acceptable salts thereof;

provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa14, Xaa$_{15}$, Xaa$_{16}$, Xaa$_{17}$, Xaa$_{19}$, Xaa$_{20}$, Xaa$_1$, Xaa$_{24}$, Xaa$_{25}$, Xaa$_{26}$, Xaa$_{27}$, and Xaa$_{28}$ are Ala; and provided also that the compound is not exendin-3 [SEQ ID NO. 1 ] or exendin-4 [SEQ ID NO. 2].

In other aspects of the invention, the increase in urine flow is accompanied by an increase in sodium excretion in said individual. In most preferred aspects, the increase in urine flow does not increase urinary potassium concentration in said individual.

In other embodiments of the invention, a method is provided for decreasing the concentration of potassium in the urine of an individual comprising administering to said individual a therapeutically effective amount of an exendin or an exendin agonist.

In yet another aspect of the invention, a method is provided for preventing or alleviating a condition or disorder associated with toxic hypervolemia in an individual, comprising administering to said individual a therapeutically effective amount of an exendin or an exendin agonist.

By condition or disorder associated with toxic hypervolemia is meant any condition or disorder in a subject that is either caused by, complicated by, or aggravated by a relatively high extracellular volume. Such conditions or disorders include, but are not limited to, renal failure, congestive heart failure, nephrotic syndrome, pulmonary edema, cirrhosis, and hypertension.

The present invention also provides a method of inducing rapid diuresis in an individual comprising administering to said individual a therapeutically effective amount of an exendin or an exendin agonist. One preferred use of this method is in preparation of a patient for a surgical procedure where a reduction in extracellular volume is desired, such as in some ocular surgical procedures or in some neurosurgical procedures. Thus, the present invention provides a method of preparing an individual for a surgical procedure comprising administering to said individual a therapeutically effective amount of an exendin or an exendin agonist. Preferably, said exendin or exendin agonist is administered to said individual before said surgical procedure.

In other preferred aspects, a method is provided for increasing renal plasma flow and glomerular filtration rate in an individual comprising administering to said individual a therapeutically effective amount of an exendin or an exendin agonist.

In yet other preferred aspects, a method is provided for treating pre-eclampsia or eclampsia of pregnancy in an individual comprising administering to said individual a therapeutically effective amount of an exendin or an exendin agonist.

The preferred mode of administration of said exendin or exendin agonist is by peripheral (subcutaneous or intravenous) administration. Preferably, said exendin or exendin agonist is administered subcutaneously. Preferably, about 1 g–30 g to about 10–20 mg of the exendin or exendin agonist is administered per dose. More preferably, about 30 g to about 10 mg, or about 300 g to about 5 mg of the exendin or exendin agonist is administered per dose. Most preferably, about 30 g to about 1 mg of the exendin or exendin agonist is administered per dose.

In other preferred aspects, said peripheral administration is selected from the group consisting of buccal, nasal, pulmonary, oral, intraocular, rectal, and transdermal administration.

The present invention also provides pharmaceutical compositions for use in the treatment of conditions or disorders associated with hypervolemia comprising a therapeutically effective amount of an exendin or exendin agonist in association with a pharmaceutically acceptable carrier.

In yet other aspects, the invention provides pharmaceutical compositions for use in increasing urine flow in an individual comprising a therapeutically effective amount of an exendin or exendin agonist in association with a pharmaceutically acceptable carrier.

In further aspects, the invention provides pharmaceutical compositions for use in treating pre-eclampsia or eclampsia of pregnancy in an individual comprising a therapeutically effective amount of an exendin or exendin agonist in association with a pharmaceutically acceptable carrier.

Preferably, these pharmaceutical compositions comprise exendin-3. More preferably, these pharmaceutical compositions comprise exendin-4.

Preferably, these pha rmaceutical compositions comprise an exendin agonist of formula I [SEQ ID NO. 4].

The present invention is also directed to novel methods for increasing urine flow comprising the administration of GLP-1.

In one embodiment the invention features a method of increasing urine flow in an individual comprising administering to the individual a therapeutically effective amount of GLP-1 or GLP-1 agonist. By GLP-1 agonist is meant a compound that mimics the effects of GLP-1 on increasing urine flow, increasing sodium excretion, and/or decreasing urinary potassium concentration, by binding to the receptor or receptors where GLP-1 causes this effect. Certain GLP-1 agonists are described in Chen et al., U.S. Pat. No. 5,512,549, issued Apr. 30, 1996, entitled Glucagon-Like Insulinotropic Peptide Analogs, Compositions and Methods of Use. Other GLP-1 agonists are described in Johnson et al., U.S. Pat. No. 5,574,008, issued Nov. 12, 1996, entitled, Biologically Active Fragments of Glucagon-Like Insulinotropic Peptide. Still other GLP-1 agonists are described in Buckley et al., U.S. Pat. No. 5,545,618, issued Aug. 13, 1996, entitled GLP-1 Analogs Useful for Diabetes Treatment. All three referenced U.S. patents are incorporated herein by this reference.

In other aspects of the invention, the increase in urine flow is accompanied by an increase in sodium excretion in said individual. In most preferred aspects, the increase in urine flow does not increase urinary potassium concentration in said individual.

In other embodiments of the invention, a method is provided for decreasing the concentration of potassium in the urine of an individual comprising administering to said individual a therapeutically effective amount of GLP-1 or a GLP-1 agonist.

In yet another aspect of the invention, a method is provided for preventing or alleviating a condition or disorder associated with toxic hypervolemia in an individual, comprising administering to said individual a therapeutically effective amount of GLP-1 or a GLP-1 agonist.

The present invention also provides a method of inducing rapid diuresis in an individual comprising administering to said individual a therapeutically effective amount of GLP-1 or a GLP-1 agonist. One preferred use of this method is in preparation of patient for surgical procedures where a reduction in extracellular volume is desired, such as in some ocular surgical procedures and some neurosurgical procedures. Thus, the present invention provides a method of preparing an individual for a surgical procedure comprising administering to said individual a therapeutically effective amount of GLP-1 or a GLP-1 agonist. Preferably, said GLP-1 or GLP-1 agonist is administered to said individual before said surgical procedure.

In other preferred aspects, a method is provided for increasing renal plasma flow and glomerular filtration rate in an individual comprising administering to said individual a therapeutically effective amount of GLP-1 or GLP-1 agonist.

In yet other preferred aspects, a method is provided for treating pre-eclampsia or eclampsia of pregnancy in an individual comprising administering to said individual a therapeutically effective amount of GLP-1 or GLP-1 agonist.

The preferred mode of administration of said GLP-1 or GLP-1 agonist is by peripheral administration. Preferably, said GLP-1 or GLP-1 agonist is administered subcutaneously or intravenously. Preferably, about 1 g–30 g to about 10–20 mg of GLP-1 or GLP-1 agonist is administered per dose. More preferably, about 30 g to about 10 mg, or about 300 g to about 5 mg of GLP-1 or GLP-1 agonist is administered per dose. Most preferably, about 30 g to about 1 mg of GLP-1 or GLP-1 agonist is administered per dose.

In other preferred aspects, said peripheral administration is selected from the group consisting of buccal, nasal, pulmonary, oral, intraocular, rectal, and transdermal administration.

The present invention also provides pharmaceutical compositions for use in the treatment of conditions or disorders associated with hypervolemia comprising a therapeutically effective amount of GLP-1 or a GLP-1 agonist in association with a pharmaceutically acceptable carrier.

In yet other aspects, the invention provides pharmaceutical compositions for use in increasing urine flow in an individual comprising a therapeutically effective amount of GLP-1 or a GLP-1 agonist in association with a pharmaceutically acceptable carrier.

In further aspects, the invention provides pharmaceutical compositions for use in treating pre-eclampsia or eclampsia of pregnancy in an individual comprising a therapeutically effective amount of GLP-1 or a GLP-1 agonist in association with a pharmaceutically acceptable carrier.

The present invention also features methods for inducing an inotropic effect in an individual comprising administering a therapeutically effective amount of an exendin or an exendin agonist, or GLP 1 or a GLP 1 agonist. Thus, in one aspect, is provided a method for increasing cardiac contractility in an individual comprising administering a therapeutically effective amount of an exendin, an exendin agonist, GLP-1 or a GLP-1 agonist.

In a related aspect, a method is provided for treating a condition or disorder that can be alleviated by increasing cardiac contractility in an individual comprising administering a therapeutically effective amount of an exendin, an exendin agonist, GLP-1 or a GLP-1 agonist. Such conditions or disorders include congestive heart failure, pulmonary and systemic edema, and renal failure. Preferably, said condition or disorder is congestive heart failure.

Preferably, said exendin is to be used in those methods exendin-3. More preferably, said exendin is exendin-4.

Preferably, the exendin agonist to be used in those methods is an exendin agonist of formula (I) [SEQ ID NO. 4].

In preferred aspects, said exendin, exendin agonist, GLP-1, or a GLP-1 agonist to be used in these methods is administered peripherally using the doses described herein.

Preferably, said peripheral administration is selected from the group consisting of buccal, nasal, pulmonaryv, oral, intraocular, rectal, and transdermal administration.

In another preferred aspect, said exendin, exendin agonist, GLP-1, or a GLP-1 agonist is administered subcutaneously or intravenously.

Also provided in the present invention are pharmaceutical compositions for use in the treatment of a condition or disorder that can be alleviated by increasing cardial contractility comprising a therapeutically effective amount of an exendin, an exendin agonist, GLP-1 or a GLP-1 agonist in association with a pharmaceutically acceptable carrier. Preferably, said exendin is exendin-3. More preferably, said exendin is exendin-4. Preferably, these pharmaceutical compositions comprise an exendin agonist of formula I [SEQ ID NO. 4].

DETAILED DESCRIPTION OF THE INVENTION

Figure 1A:
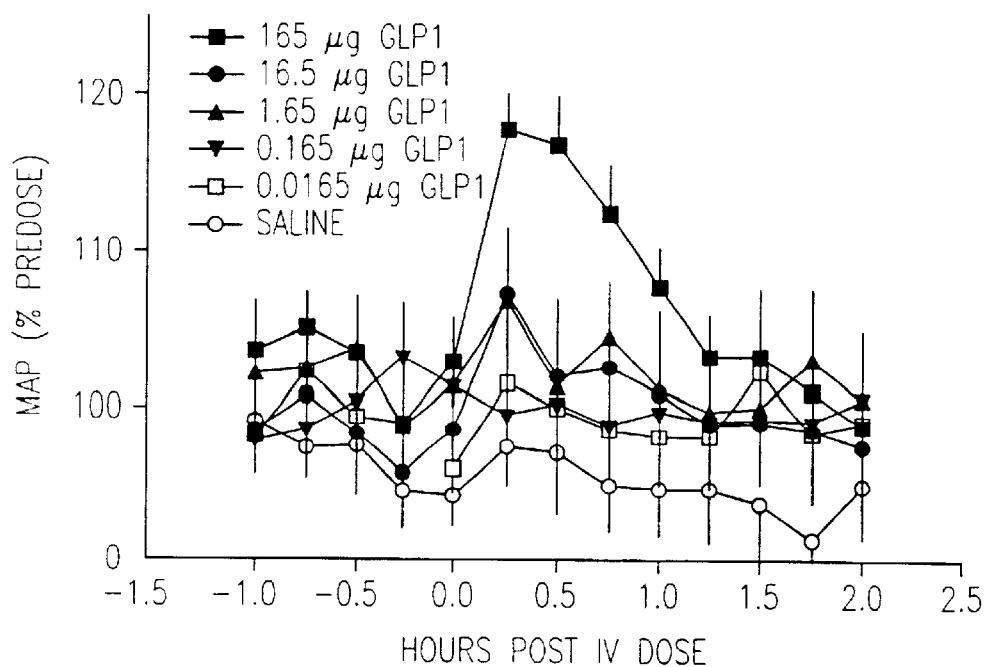
FIG. 1(A–B) is a graphical depiction of the response of mean arterial pressure (MAP) to GLP-1. (A) MAP is presented as % of predose values measured over the 30 minutes prior to drug administration; (B) Dose-response curve for effects of GLP-1 of MAP. The response plotted is the incremental area under the curve from 0 to 2 hours after the bolus dose.

The exendins, GLP-1, and analogs and agonists thereof of this invention are useful in view of their pharmacological properties. Activity as exendin or GLP-1 analogs or agonists can be indicated by activity in the assays described below. Effects of exendins or GLP-1 agonists thereof on reducing food intake can be identified, evaluated, or screened for, using the methods described in the Examples below, or other methods known in the art for determining effects on urine flow, or sodium or potassium excretion.

Although exendin-4 was found to have a hypertensive effect, when administered in conjunction with an agent that regulated blood pressure, the diuretic effect was still evident, indicating a diuretic effect of exendin-4 that was not entirely attributable to its hypertensive effect.

Exendin Agonist Compounds

Exendin agonist compounds include those described in U.S. Provisional Patent Application Nos. 60/055,404; 60/066,029; and 60/065,442. Preferred exendin agonist compounds include peptide compounds of the formula (I) [SEQ ID NO. 4]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
—NH$_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$,
Gly Gly $Xaa_{31}$ Ser Ser Gly Ala $Xaa_{36}$ $Xaa_{37}$ $Xaa_{38}$-$Z_2$, or
Gly Gly Xaa31 Ser Ser Gly Ala $Xaa_{36}$ $Xaa_{37}$ $Xaa_{38}$ $Xaa_{39}$-$Z_2$;
wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; $Xaa_{39}$ is Ser, Thr or Tyr; and $Z_2$ is —OH or —NH$_2$; and pharmaceutically acceptable salts thereof;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and provided also that the compound is not exendin-3 or exendin-4.

Preferred N-alkyl groups for N-alkylglycine N-alkylpentylglycine and N-alkylalanine include lower alkyl groups preferably of 1 to about 6 carbon atoms, more preferably of 1 to 4 carbon atoms. Suitable compounds include those identified in Examples 4–64 [SEQ ID NOS. 5 to 65], as well as those compounds identified in Examples 65 and 66.

Preferred exendin agonist compounds include those wherein $Xaa_1$ is His or Tyr. More preferably $Xaa_1$ is His.

Preferred are those compounds wherein $Xaa_2$ is Gly.

Preferred are those compounds wherein $Xaa_{14}$ is Leu, pentylglycine or Met.

Preferred compounds are those wherein $Xaa_{25}$ is Trp or Phe.

Preferred compounds are those where $Xaa_6$ is Phe or naphthylalanine; $Xaa_{22}$ is Phe of naphthylalanine and $Xaa_{23}$ is Ile or Val.

Preferred are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —NH$_2$.
Preferably $Z_2$ is —NH$_2$.

According to one aspect, preferred are compounds of formula (I) wherein $Xaa_1$ is His or Tyr, more preferably His; $Xaa_2$ is Gly; $Xaa_6$ is Phe or naphthylalanine; $Xaa_{24}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —NH$_2$.

According to an especially preferred aspect, especially preferred compounds include those of formula (I) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or nephthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_1$, is Ala or Leu; $Xaa_{22}$ is Phe or naphthylaianine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Especially preferred compounds include those having the amino acid sequence of SEQ ID NOS. 6–27.

According to an especially preferred aspect, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative degration, both in vitro and in vivo, as well as during synthesis of the compound.

Definitions

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine. N-methylvaline, naphthalanine, norvaline, norleucine, omithine, pentylglycine, pipecolic acid and thioproline. Amino acid analogs include the natural and unnatural amino acids which are chemically blocked, reversibly or irreversibly, or modified on their N-termninal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid. N-ethylglycine is an amino acid analog of glycine; or alanine carboxamide is an amino acid analog of alanine.

The terrn "amino acid residue" refers to radicals having the structure: (1) —C(O)—R—NH—, wherein R typically is —CH(R)—, wherein R is an amino acid side chain, typically H or a carbon containing substitutent; or (2)

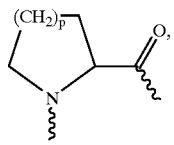

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds described herein derived from the combination of such compounds and an organic or inorganic acid. In practice the use of the salt form amounts to use of the base form. The compounds are useful in both free base and salt form.

In addition, the following abbreviations stand for the following:

"ACN" or "CH$_3$CN" refers to acetonitrile.
"Boc", "tBoc" or "Tboc" refers to t-butoxy carbonyl.
"DCC" refers to N,N'-dicyclohexylcarbodiimide.
"Fmoc" refers to fluorenylmethoxycarbonyl.
"HBTU" refers to 2-(1H-benzotriazol-1-yl)-1,1,3,3,-tetramethyluronium hexaflurophosphate.
"HOBt" refers to 1-hydroxybenzotriazole monohydrate.
"homoP" or "hPro" refers to homoproline.
"MeAla" or "Nime" refers to N-methylalanine.
"naph" refers to naphthylalanine.
"pG" or pGly" refers to pentylglycine.
"tBuG" refers to tertiary-butylglycine.
"ThioP" or "tPro" refers to thioproline.
3Hyp" refers to 3-hydroxyproline
4Hyp" refers to 4-hydroxyproline
NAG" refers to N-alkylglycine
NAPG" refers to N-alkylpentylglycine
"Norval" refers to norvaline
"Norleu" refers to norleucine Preparation of Compounds Compounds such as the exendins and exendin agonists described herein may be prepared using standard solid-phase peptide synthesis techniques and preferably an automated or semiautomated peptide synthesizer. Typically, using such techniques, an —N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The -N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenyl-methoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City. Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville. Ky.).

Peptides may be purified by RP-HPLC (preparative and analytical) using a Waters Delta Prep 3000 system. A C4, C8 or C18 preparative column (10$\mu$, 2.2×25 cm; Vydac, Hesperia, Calif.) may be used to isolate peptides, and purity may be determined using a C4, C8 or C18 analytical column (5$\mu$, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried out on a VG-Trio machine.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356–377 (1986).

Exendin or GLP-1 agonist analogs or derivatives are included within the methods of the present invention. Analogs or derivatives are functional variants of an exendin or to GLP-1 having similar amino acid sequence and retaining, to some extent, the increase in urine flow, increase in sodium excretion and/or decrease in potassium-excretion, activities of the related exendin or GLP-1 or agonists thereto. By a functional variant is meant the derivative has an activity that can be substituted for one or more activities of a particular exendin or GLP-1 or an agonist thereto. Preferred functional variants retain all of the activities of a particular exendin or GLP-1 or an agonist thereto, however, the functional variant may have an activity that, when measured quantitatively, is stronger or weaker, as measured in functional assays, for example, such as those disclosed herein. Preferred functional variants have activities that are within about 1% to about 10,000% of the activity of the related exendin, GLP-1, or agonist thereto, more preferably between about 10% to about 1000%, and more preferably within about 50% to about 500%. Derivatives have at least about 50% sequence similarity, preferably about 70%, more preferably about 90%, and even more preferably about 95% sequence similarity to the related exendin or GLP-1, or agonist thereto. "Sequence similarity" refers to "homology" observed between amino acid sequences in two different polypeptides, irrespective of polypeptide origin.

The ability of the derivative to retain some activity can be measured using techniques described herein. Derivatives include modification occurring during or after translation, for example, by phosphorylation, glycosylation, crosslinking, acylation, proteolytic cleavage, linkage to an antibody molecule, membrane molecule or other ligand (see Ferguson et al., *Annu. Rev. Biochem.* 57:285–320, 1988).

Derivatives can be produced using standard chemical techniques and recombinant nucleic acid molecule techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Sambrook, et al., Molecular Cloning, Cold Spring Harbor Laboratory Press (1989).

The compounds referenced above form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds described above are useful in view of their pharmacological properties. In particular, the compounds of the invention possess activity as agents to increase urine flow, increase sodium excretion and decrease potassium excretion, and to alleviate conditions or diseases associated with hypertoxic volemia.

Compositions useful in the invention may conveniently be provided in the form of formulations suitable for parenteral (including intravenous, intramuscular and subcutaneous) or nasal or oral administration. In some cases, it will be convenient to provide an exendin or exendin agonist and another food-intake-reducing, plasma glucose-lowering or plasma lipid-lowering agent, such as amylin, an amylin agonist, a CCK, or a leptin, in a single composition or solution for administration together. In other cases, it may be more advantageous to administer the additional agent separately from said exendin or exendin agonist. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 3.0 to 8.0, preferably at a pH of about 3.5 to 5.0. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an exendin or exendin agonist, for example, exendin-3, and/or exendin-4. Therapeutically effective amounts of an exendin or exendin agonist for use in increasing urine flow are those that increase urine flow at a desired rate and level. As will be recognized by those in the field, an effective amount of therapeutic agent will vary with many factors including the age and weight of the patient, the patient's physical condition and other factors.

The effective dose of the compounds will typically be in the range of 1–30 μg to about 10–20 mg, preferably about 30 μg to 10 mg and more preferably about 300 μg to 5 mg, most preferably 30 μg to about 1 mg. The exact dose to be administered is determined by the attending clinician and is dependent, for example, upon where the particular compound lies within the above quoted range. Administration should begin whenever a diuretic effect is desired, for example, at the first sign of symptoms or shortly after diagnosis of renal failure, congestive heart failure, nephrotic syndrome, pulmonary edema, cirrhosis, hypertension eclampsia, or pre-eclampsia. Administration may be by injection, preferably subcutaneous or intramuscular. Orally active compounds may be taken orally, however dosages should be increased 5–10 fold.

The optimal formulation and mode of administration of compounds of the present application to a patient depend on factors known in the art such as the particular disease or disorder, the desired effect, and the type of patient. While the compounds will typically be used to treat human subjects they may also be used to treat similar or identical diseases in other vertebrates such as other primates, farm animals such as swine, cattle and poultry, and sports animals and pets such as horses, dogs and cats.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Eaxmple 1

Diuretic Effects of GLP-1 or Exendin Administration

Materials: GLP-1 and exendin-4 were purchased from Bachem, Inc., Torrance, Calif. or synthesized at Amylin Pharmaceuticals, Inc., as described herein. Blood pressure transducers/transmitters were obtained from Data Sciences, Inc.

In Vivo Studies in Anesthetized rats: Male, Harlan Sprague Dawley rats were housed at 23±1° C. in a 12:12 hour light:dark cycle (experiments being performed during the light cycle) and were fed and watered ad libitum (Diet LM-485, Teklad, Madison, Wis.). Animals weighing 325–375 gms were fasted for ~20 hours prior to experimentation.

Surgical preparation: The preparation used here was as described in Young et al., (*Drug Dev Res.* 37:231–248, 1996), but modified by the addition of unilateral ureteral cannulation. Anesthesia was induced with 5% halothane, maintained with 2% halothane during surgery and with 0.7 to 1% thereafter. Tracheotomy and cannulation of a femoral artery, saphenous vein and a single ureter were performed. The arterial line, perfused with heparinized saline (2U/ml), was used for blood sampling and pressure measurement (Spectramed P23XL transducer, Model 13–4615–58 amplifier, Gould, Cleveland, Ohio). The venous line was used for drug administration. Total saline infusion rate was kept at 4 mL/hr. Colonic temperature was measured and controlled using a thermistor probe/controller (Model 73A, YSI, Yellow Springs, Ohio) and a heated operating table. Signals for mean arterial pressure were periodically sampled at 1 Hz with 12 bit precision (DataTranslation DT2801A) and recorded (Labtech Notebook).

Numerical Methods: Dose-response curves were fitted to 4-parameter logistic functions and $EC_{50}$s derived using Prism (v2.0, GraphPad Software, San Diego, Calif.). Observations are expressed as the percent of baseline, defined as the mean of measurements made in the 30 min prior to starting peptide or vehicle infusion. Data are expressed as mean±SEM, n=5–6.

Measurements: Samples of arterial blood (160 µl) were collected periodically and samples of urine were collected every 15 min. Plasma and urinary sodium and potassium concentrations were measured by ion-selective electrodes using Ciba/Corning 614 Na/K analyzer (Ciba/Corning, Inc., Medfield, Mass.). Unilateral urine flow was measured by weighing the 15-minute output of the cannulated ureter. Total urine flow was estimated as twice this amount.

Figure 3A:
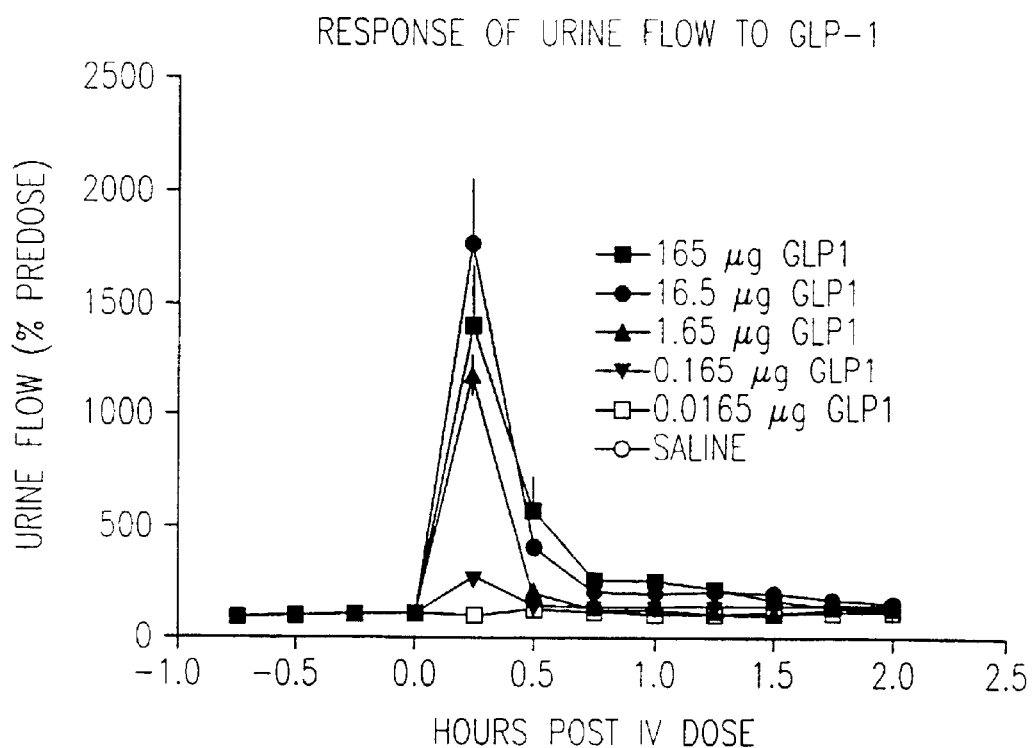
FIG. 3(A–B) is a graphical depiction of the response of urine flow to intravenous bolus doses of GLP-1. (A) Urine flow was measured at 15 minute intervals and presented as % of predose values measured over the 30 minutes prior to drug administration; (B) Dose-response curve for effects of GLP-1 on urine flow. The response plotted is the percent change in flow from 0 to 15 minutes after the bolus dose relative to the flow over the previous 30 minutes.
Figure 3B:
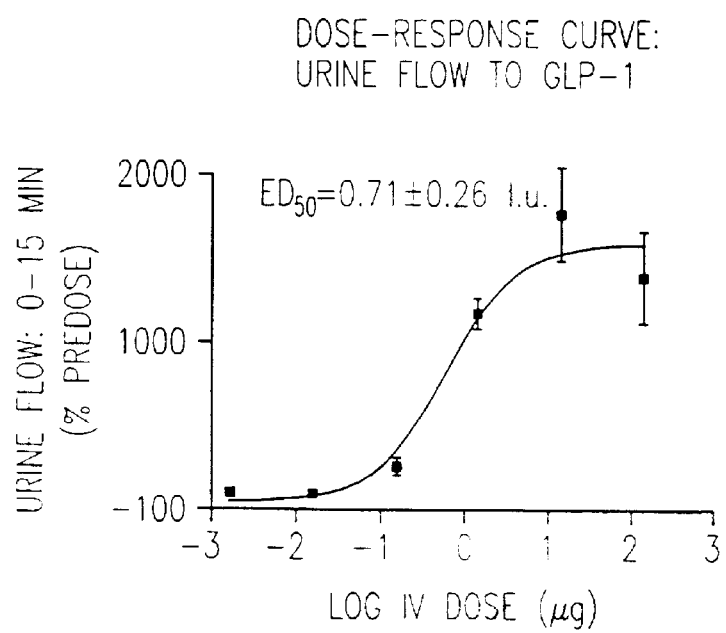
Figure 4A:
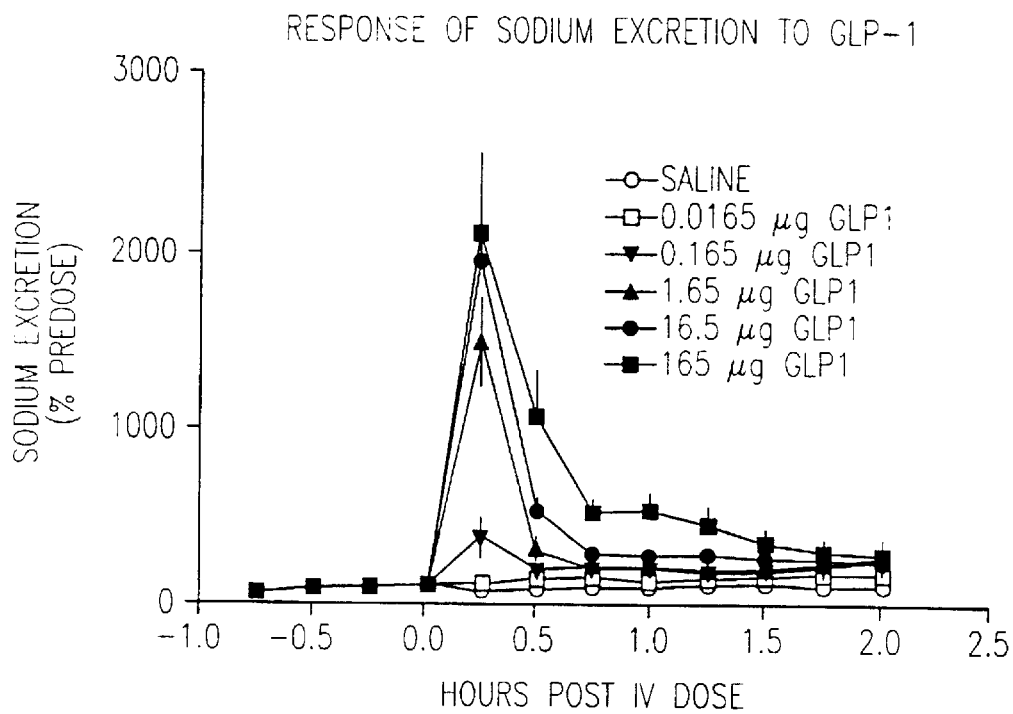
FIG. 4(A–B) is a graphical depiction of the response of sodium excretion to intravenous bolus doses of GLP-1. (A) Sodium excretion was measured at 15 minute intervals and presented as % of predose values measured over the 30 minutes prior to drug administration; (B) Dose-response curve for effects of GLP-1 on sodium excretion. The response plotted is the percent change in sodium excretion from 0 to 15 minutes after the bolus dose relative to excretion over the previous 30 minutes.
Figure 4B:
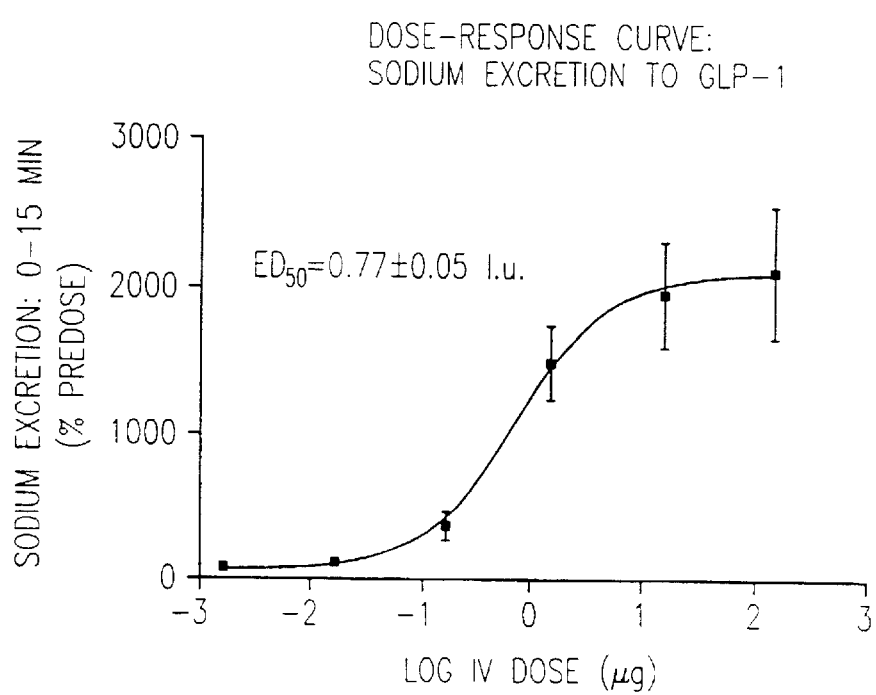
Figure 5A:
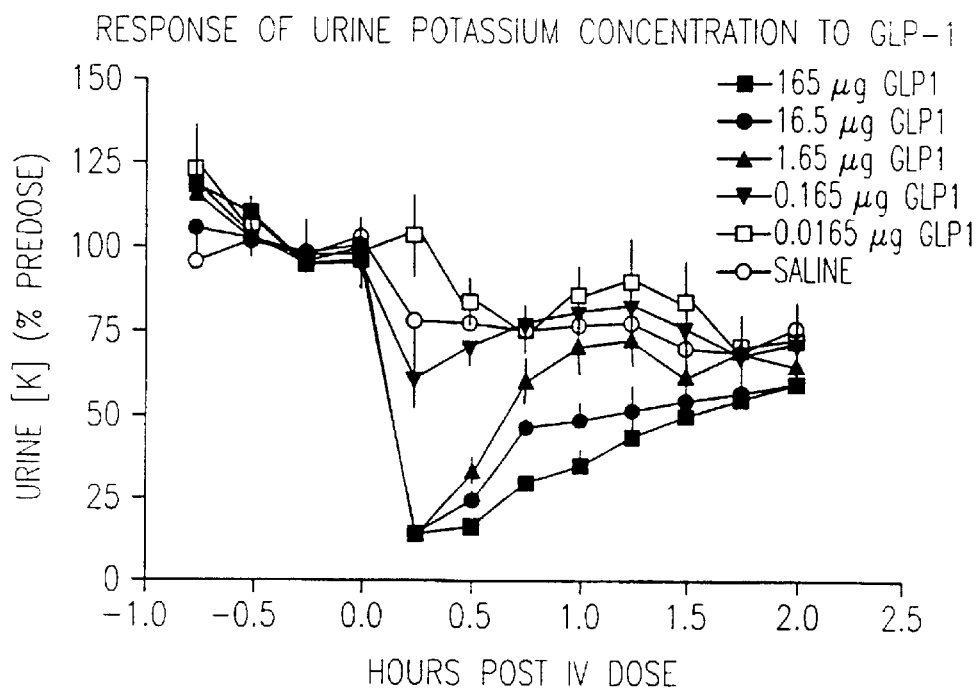
FIG. 5(A–B) is a graphical depiction of the response of urinary potassium concentration to intravenous bolus doses of GLP-1. (A) Urinary potassium concentration was measured at 15 minute intervals and presented as % of predose values measured over the 30 minutes prior to drug administration; (B) Dose-response curve for effects of GLP-1 on urinary potassium concentration. The response plotted is the percent change in urinary potassium concentration from 0 to 15 minutes after the bolus dose relative to the urinary potassium concentration over the previous 30 minutes.
Figure 5B:
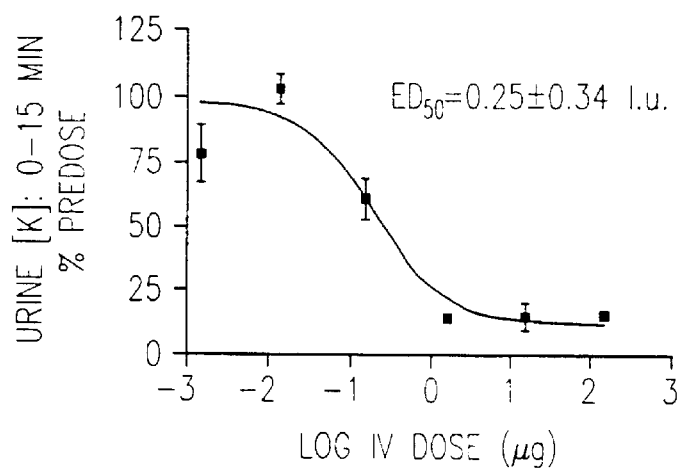
Figure 8A:
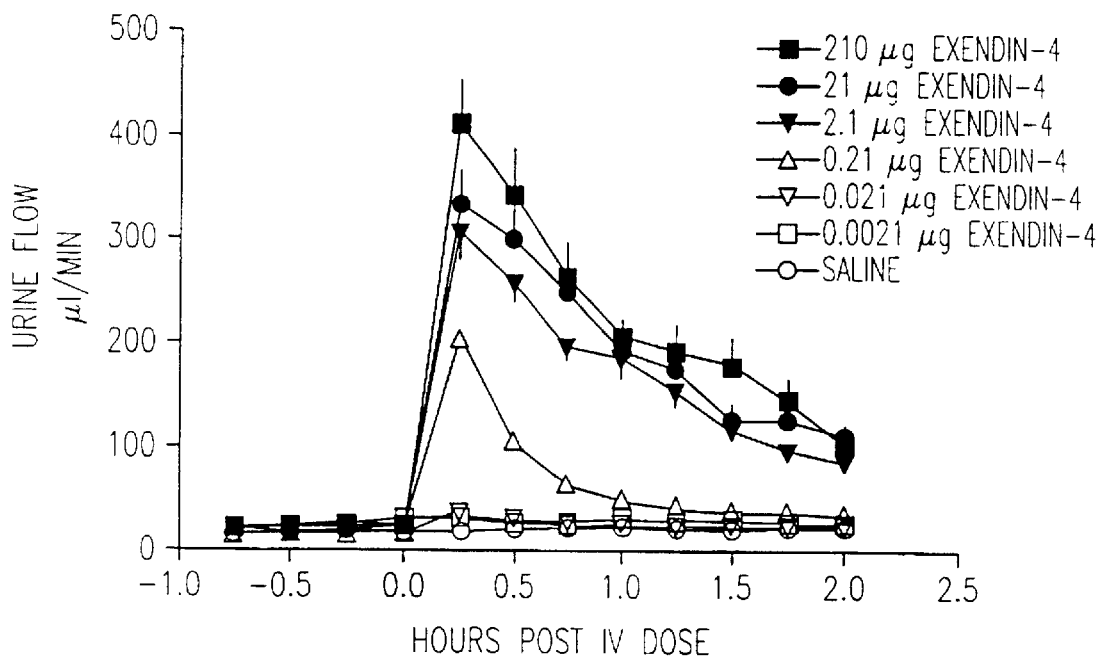
FIG. 8(A–B) is a graphical depiction of the response of urine flow to intravenous bolus doses of exendin-4. (A) Urine flow was measured at 15 minute intervals; (B) Dose-response curve for effects of exendin-4 on urine flow. The response plotted is urine flow from 0 to 15 minutes after the bolus dose.
Figure 8B:
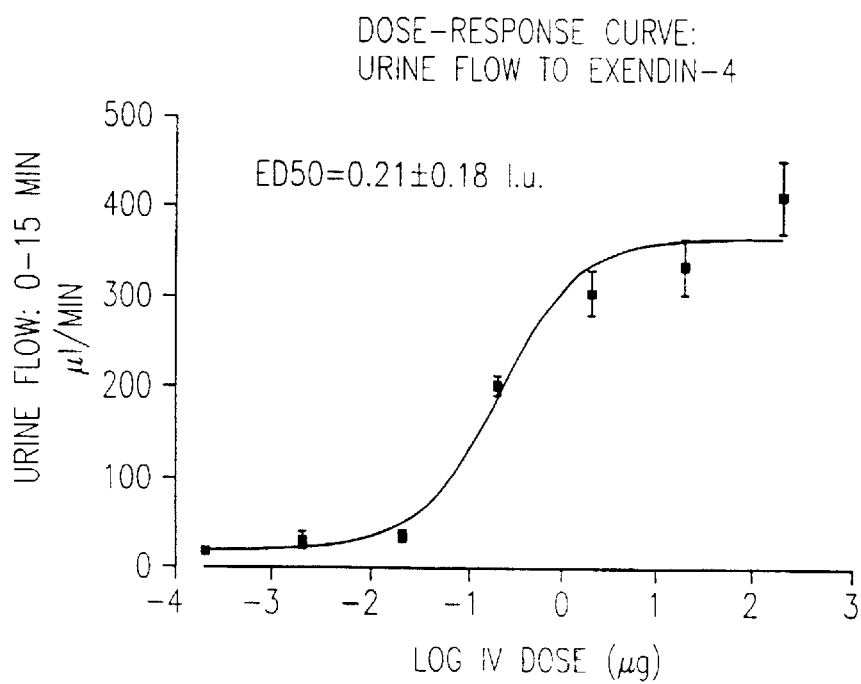
Figure 9A:
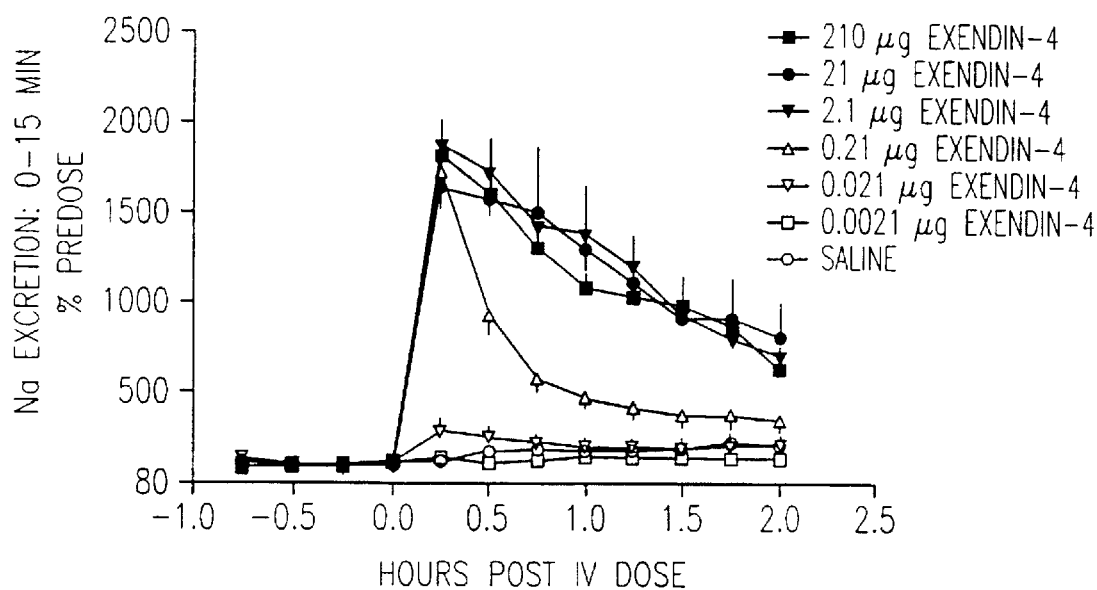
FIG. 9(A–B) is a graphical depiction of the response of sodium excretion to intravenous bolus doses of exendin-4. (A) Sodium excretion was measured at 15 minute intervals and presented as % of predose values measured over the 30 minutes prior to drug administration; (B) Dose-response curve for effects of exendin-4 on sodium excretion. The response plotted is the percent change in sodium excretion from 0 to 15 minutes after the bolus dose relative to excretion over the previous 30 minutes.
Figure 9B:
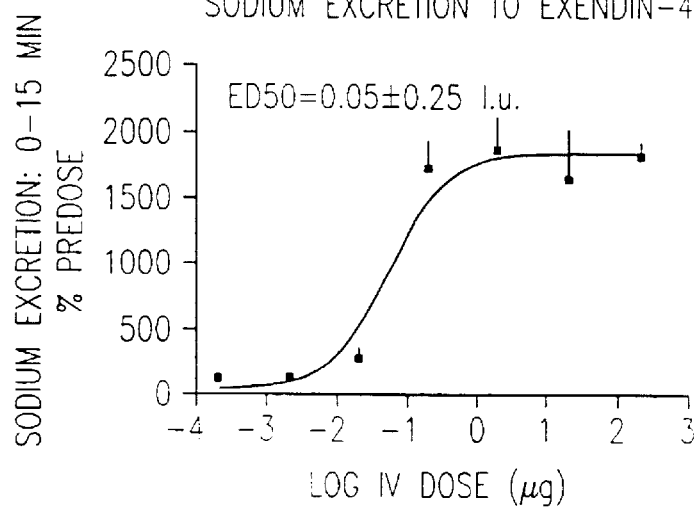
Figure 10A:
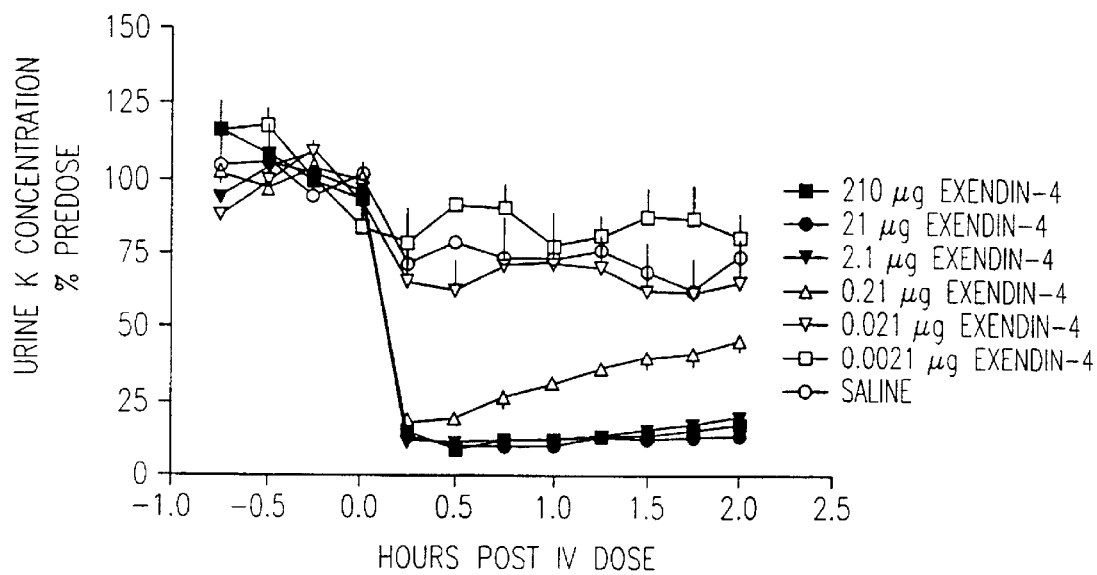
FIG. 10(A–B) is a graphical depiction of the response of urinary potassium concentration to intravenous bolus doses of exendin-4. (A) Urinary potassium concentration was measured at 15 minute intervals and presented as % of predose values measured over the 30 minutes prior to exendin-4 administration; (B) Dose-response curve for effects of exendin on urinary potassium concentration. The response plotted is the incremental area under the curve from 0 to 2 hours after the bolus dose.
Figure 10B:
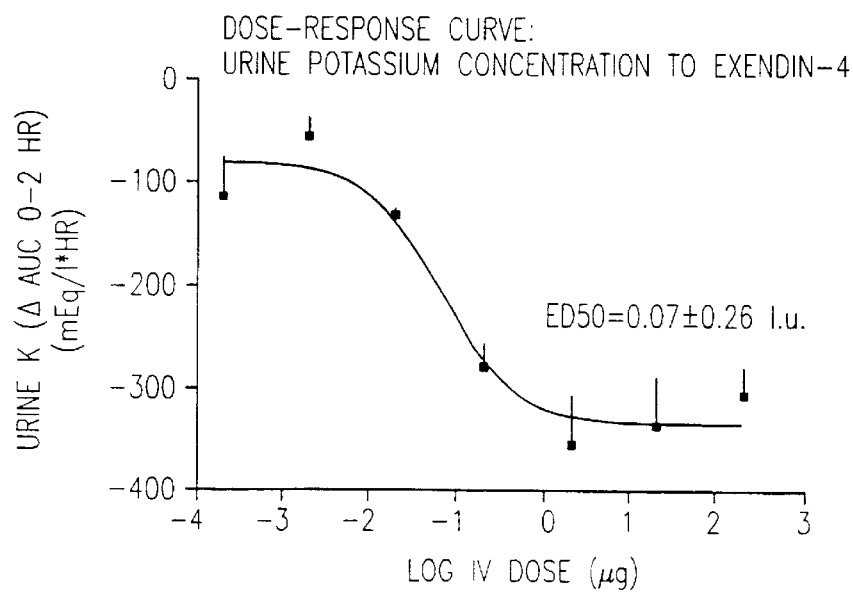

Treatments: To obtain dose-responses, peptides were dissolved in 0.15 M NaCl and administered as 0.1 ml bolus. Administration of GLP-1 had a strong effect on increasing urine flow ($ED_{50}$=0.71 µg±0.26 log units). The maximum response as percent of predose urine flow was 1764±281% at 15 minutes for the 16.5 µg dose (FIGS. 3A–B). Administration of GLP-1 also increased sodium excretion (FIGS. 4A–B). However, GLP-1 significantly decreased the excretion of potassium (FIGS. 5A–B) ($ED_{50} \geq 0.25$ µg±34 log units with a maximal fall to 13.9±1.7% of predose concentrations at a dose of 1.65 µg). Administration of exendin-4 also increased urine flow (FIGS. 8A–B). The $ED_{50}$ was 0.12 µg±0.18 log units and the maximum response as percent of predose urine flow was 2160±470% at 15 minutes for the 21 µg dose. Administration of exendin also increased sodium excretion (FIGS. 9A–B). However, the excretion of potassium was decreased (FIGS. 10A–B). The $ED_{50}$ was 0.07 µg±0.26 log units with a maximal decrease to 9.6±1.4% of predose concentrations at a dose of 21 µg.

Example 2
Measurement of Arterial Blood Pressure and dP/dt in Conscious Rats by Telemetra After Administration of GLP-1 or Exendin-4:

Insertion of Transducers: Male, Harlan Sprague Dawley rats were anesthetized with halothane and the abdominal aorta exposed after laparotomy. According to procedures detailed in the "Pressure Telemetry" manual from Data Sciences Inc., pressure transducer/transmitters were secured in place on the abdominal wall with the catheter tip in the abdominal aorta ~2 mm above bifurcation. Following closure, the animals then recovered to allow at least 7 days of stable recordings. Baseline data were collected during the 7+ days after surgery.

Measurement of blood pressure and dP/dt: After obtaining a stable baseline, rats received an intraperitoneal (ip) injection of GLP-1, exendin or vehicle alone (NaCl). The transmitted signals were recorded via telemetry and stored on a personal computer. Rate of pressure change, dP/dt, was calculated by software provided by Data Sciences.

Figure 1B:
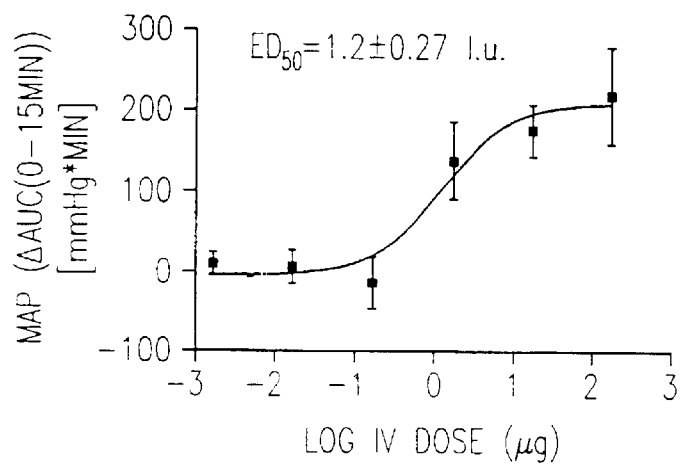
Figure 2:
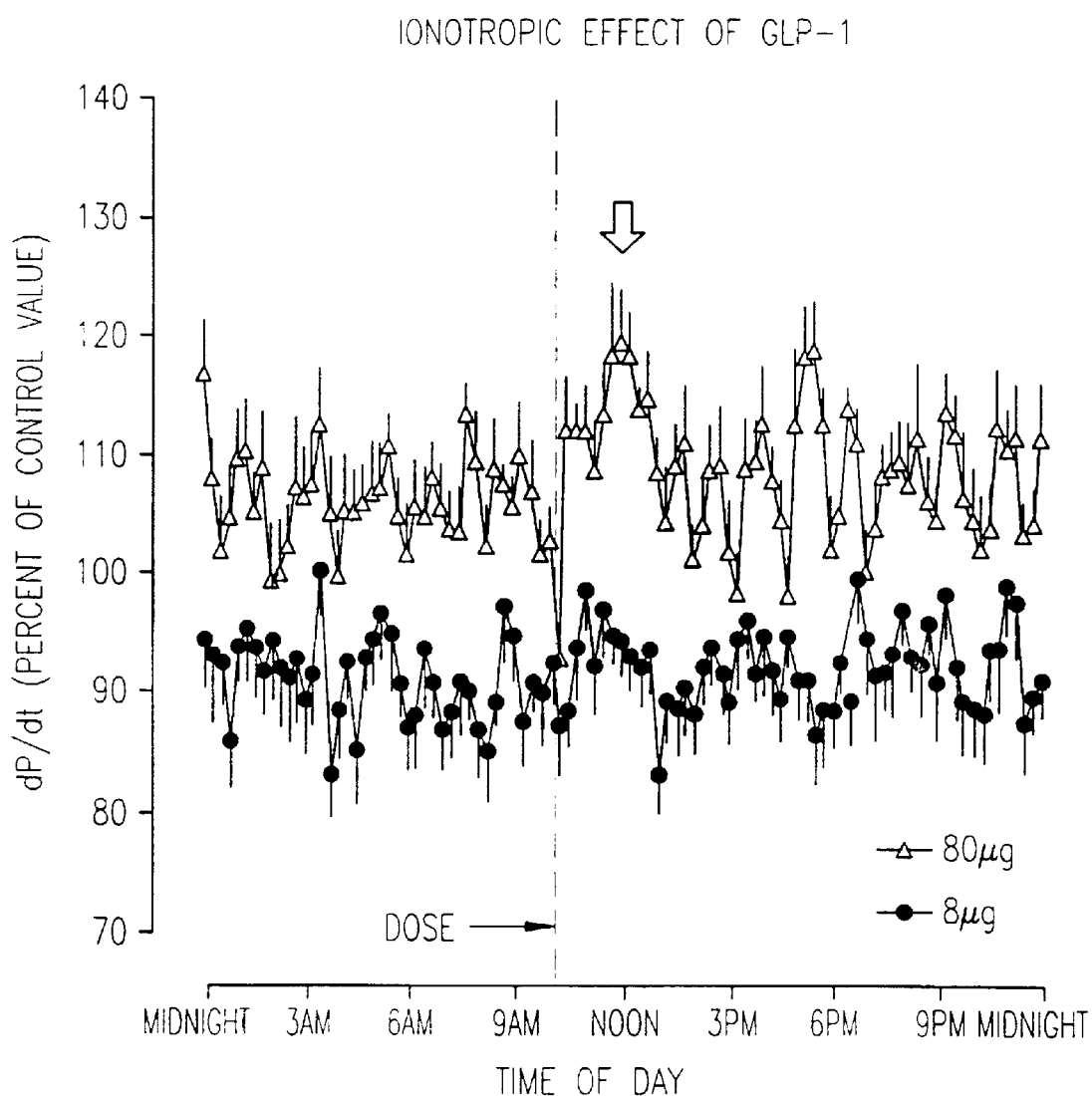
FIG. 2 is a graphical depiction of the inotropic response to GLP-1. The rate of change of blood pressure (dP/dt) is indicative of cardiac contractility, which increased in response to a subcutaneous injection of GLP-1 given to conscious rats.

GLP-1: Animals received a single intraperitoneal (ip) injection of saline or GLP-1 (100 µl), n=7–8. FIGS. 1A–B depict the increase in mean arterial pressure after GLP-1 administration. FIG. 2 depicts the increase in cardiac contractility after GLP-1 administration.

Figure 6A:
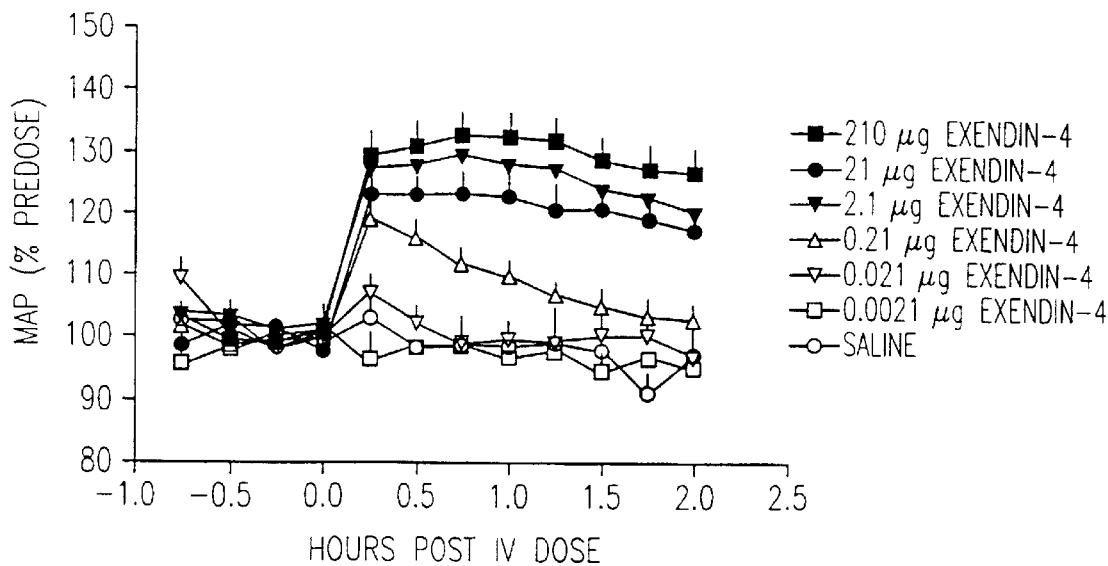
FIG. 6(A–B) is a graphical depiction of the response of mean arterial pressure (MAP) to exendin 4. (A) MAP is presented as % of predose values measured over the 30 minutes prior to drug administration; (B) Dose-response curve for effects of exendin on MAP. The response plotted is the incremental area under the curve from 0 to 2 hours after the bolus dose.
Figure 6B:
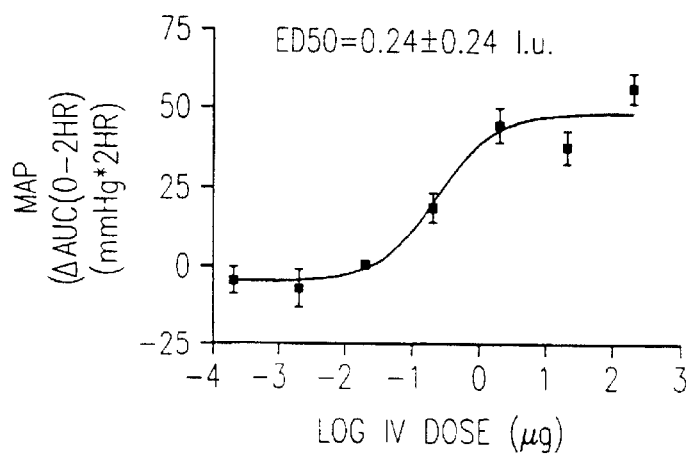
Figure 7:
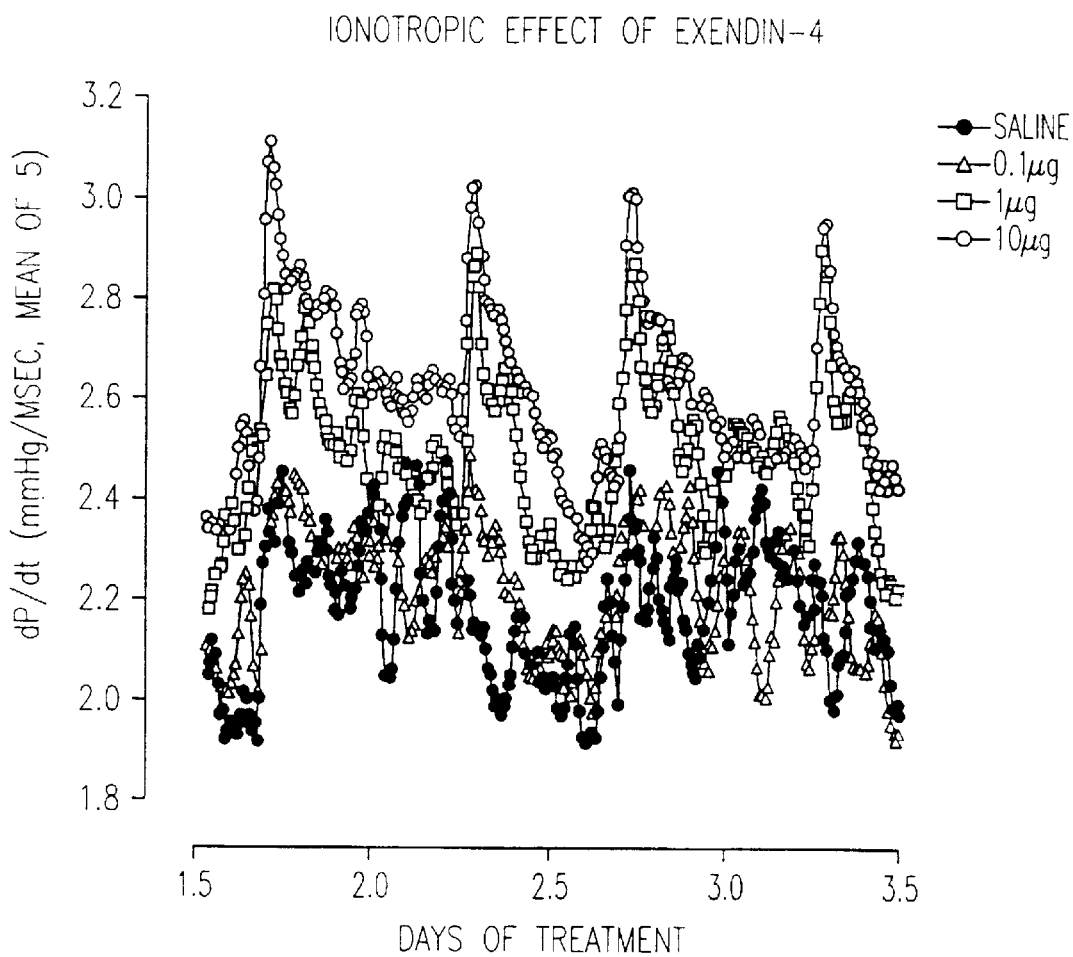
FIG. 7 is a graphical depiction of the inotropic response to exendin-4. The rate of change of blood pressure (dP/dt) is indicative of cardiac contractility, which increased in response to a subcutaneous injection of exendin-4 given to conscious rats.

Exendin-4: Exendin-4 or saline (250 µl) was given twice daily (bid) by ip injection for five days, n=8 for saline and 5–6 for the exendin groups. FIGS. 6A–B depict the increase in mean arterial pressure after exendin-4 administration. FIG. 7 depicts the increase in cardiac contractility after exendin-4 administration.

Example 3
Cardiovascular Actions of Exendin-4 or GLP-1 Measured Using Transonic Flow Probes in Anesthetised Rats:

Materials, animal husbandry and cannulation under anesthesia: Materials animal husbandry and cannulation under anesthesia were as described in Example 1. Male Sprague Dawley rats (350–450 g), anesthetised with halothane, were cannulated via the saphenous vein (for peptide injection) and femoral artery (for arterial pressure measurement).

Surgery: A transit time flow probe (2 mm, 2SB, Transonic Systems Inc., Ithaca N.Y.) was placed around the abdominal aorta, distal to renal, mesenteric and iliac artery branches.

Measurements: The flow probe was connected to a Transonic TS-206 dual channel flowmeter for measurement of abdominal aortic blood flow. Heart rate was recorded using standard ECG electrodes. Peptides or vehicle (saline) were injected intravenously in a total volume of 100 µL over 1–2 minutes. Mean arterial pressure (MAP), heart rate (HR) and mean aortic blood flow, were recorded every second using Labtek Notebook data acquisition software over the experimental period. Aortic conductance (flow/MAP; mL/min/mmHg) and stroke volume (flow/HR: mL/min per beats/min=mL) were then derived.

Treatments: Exendin-4 was injected in doses of 0.021, 0,21, 2,1 and 21 µg, and GLP-1 was injected in doses of 0.0165, 0.165, 1.65 and 16.5 µg after a 20 minute control period.
Results:

GLP-1: GLP-1 at a dose of 16.5 µg increased mean arterial pressure by 22 mmHg within 5 minutes of administration. Aortic blood flow increased by 57% from 14 to 22 mL/min, heart rate by 17% from 360 to 420 beat/min, stroke volume by 38% from 37 to 51 µL, and aortic conductance by 50% from 0.12 to 0.18 mL/min/mmHg within 2 minutes of GLP-1 administration. Effects lasted for about 10 min.

Exendin-4: A similar pattern of effects was observed with a 0.21 µg dose of exendin-4 (~30 mmHg increase in blood pressure; 60% increase in aortic blood flow; 40% increase in heart rate; 60% increase in stroke volume; 35% increase in aortic conductance), except that effects persisted for 30–60 min. These responses, where there are large changes in aortic blood flow and lesser changes in blood pressure, are consistent with GLP-1 and exendin-4 having inotropic (cardiac stimulatory) and vasodilator properties.

Example 4
Preparation of Peptide Having SEQ. ID. NO. 5

His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$ [SEQ. ID. NO. 5]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal)of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN). The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 50% Solvent B in Solvent A over 30 minutes) of the lyophilized peptide gave product peptide having an observed retention time of 18.9 minutes. Electrospray Mass Spectrometry (M): calculated 3408.0; found 3408.9.

Example 5
Preparation of Peptide Having SEQ. ID. NO. 6

His Gly Glu Gly Thr Phe Thr Ser Asp Leu Ser Lys Gln Met Glu Glu Glu Ala Val Arg Leu Phe Ile Glu Trp Leu Lys Asn-NH$_2$ [SEQ. ID. NO. 6]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 30% to 40% Solvent B in Solvent A over 30 minutes) of the lyophilized peptide gave product peptide having an observed retention time of 17.9 minutes. Electrospray Mass Spectrometry (M): calculated 3294.7; found 3294.8.

Example 6
Preparation of Peptide Having SEQ. ID. NO. 7

His Gly Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 7]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 29% to 36% Solvent B in Solvent A over 30 minutes) of the lyophilized peptide gave product peptide having an observed retention time of 20.7 minutes. Electrospray Mass Spectrometry (M): calculated 3237.6; found 3240.

Example 7
Preparation of Peptide Having SEQ. ID. NO. 8

His Ala Glu Gly Thr Phe Thr Ser Asp Leu Ser Lys Gln Leu Glu Glu Glu Ala Val Arg Leu Phe Ile Glu Phe Leu Lys Asn-NH$_2$ [SEQ. ID. NO. 8]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3251.6; found 3251.5.

Example 8
Pretparation of Peptide Having SEQ. ID. NO. 9

His Gly Glu Gly Ala Phe Thr Ser Asp Leu Ser Lys Gln Leu Glu Glu Glu Ala Val Arg Leu Phe Ile Glu Phe Leu Lys Asn-NH$_2$ [SEQ. ID. NO. 9]

The above anidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 13.1 minutes. Electrospray Mass Spectrometry (M): calculated 3207.6; found 3208.3.

Example 9
Preparation of Peptide Having SEQ. ID. NO. 10

His Gly Glu Gly Thr Ala Thr Ser Asp Leu Ser Lys Gln Leu Glu Glu Glu Ala Val Arg Leu Phe Ile Glu Phe Leu Lys Asn-NH$_2$ [SEQ. ID. NO. 10]

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.8 minutes. Electrospray Mass Spectrometry (M): calculated 3161.5; found 3163.

Example 10
Preparation of Peptide Having SEQ. ID. NO. 11

His Gly Glu Gly Thr Phe Thr Ala Asp Leu Ser Lys Gln Leu Glu Glu Glu Ala Val Arg Leu Phe Ile Glu Phe Leu Lys Asn-NH$_2$ [SEQ. ID. NO. 11]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 15.2 minutes. Electrospray Mass Spectrometry (M): calculated 3221.6; found 3222.7.

Example 11
Preparation of Peptide Havine SEQ. ID. NO. 12

His Gly Glu Gly Thr Phe Thr Ser Asp Ala Ser Lys Gln Leu Glu Glu Glu Ala Val Arg Leu Phe Ile Glu Phe Leu Lys Asn-NH$_2$ [SEQ. ID. NO. 12]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 14.3 minutes. Electrospray Mass Spectrometry (M): calculated 3195.5; found 3199.4.

Example 12

Preparation of Peptide Having SEQ. ID. NO. 13

His Gly Glu Gly Thr Phe Thr Ser Asp Leu Ala Lys Gln Leu Glu Glu Glu Ala Val Arg Leu Phe Ile Glu Phe Leu Lys Asn-NH$_2$ [SEQ. ID. NO. 13]

The above-identified amidated peptide was assembled on 4-(2'-4'-dimethoxyphenyl)-Fmoc arninomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 15.7 minutes. Electrospray Mass Spectrometry (M): calculated 3221.6; found 3221.6.

Example 13

Preparation of Peptide Having SEQ. ID. NO. 14

His Gly Glu Gly Thr Phe Thr Ser Asp Leu Ser Ala Gln Leu Glu Glu Glu Ala Val Arg Leu Phe Ile Glu Phe Leu Lys Asn-NH$_2$ [SEQ. ID. NO. 14]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems. Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 18.1 minutes. Electrospray Mass Spectrometry (M): calculated 3180.5; found 3180.9.

Example 14

Preparation of Peptide Having SEQ. ID. NO. 15

His Gly Glu Gly Thr Phe Thr Ser Asp Leu Ser Lys Ala Leu Glu Glu Glu Ala Val Arg Leu Phe Ile Glu Phe Leu Lys Asn-NH$_2$ [SEQ. ID. NO. 15]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 17.0 minutes. Electrospray Mass Spectrometry (M): calculated 3180.6; found 3182.8.

Example 15

Preparation of Peptide Having SEQ. ID. NO. 16

His Gly Glu Gly Thr Phe Thr Ser Asp Leu Ser Lys Gln Ala Glu Glu Glu Ala Val Arg Leu Phe Ile Glu Phe Leu Lys Asn-NH$_2$ [SEQ. ID. NO. 16]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 14.9 minutes. Electrospray Mass Spectrometry (M): calculated 3195.5; found 3195.9.

Example 16

Preparation of Peptide Having SEQ. ID. NO. 17

His Gly Glu Gly Thr Phe Thr Ser Asp Leu Ser Lys Gln Leu Ala Glu Glu Ala Val Arg Leu Phe Ile Glu Phe Leu Lys Asn-AH2 [SEQ. ID. NO. 17]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gnave product peptide having an observed retention time of 17.9 minutes. Electrospray Mass Spectrometry (M): calculated 3179.6; found 3179.0.

Example 17

Preparation of Peptide Haviny SEQ. ID. NO. 18

His Gly Glu Gly Thr Phe Thr Ser Asp Leu Ser Lys Gln Leu Glu Ala Glu Ala Val Arg Leu Phe Ile Glu Phe Leu Lys Asn-NH$_2$ [SEQ. ID. NO. 18]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 14.3 minutes. Electrospray Mass Spectrometry (M): calculated 3179.6; found 3180.0.

Example 18

Preparation of Peptide Having SEQ. ID. NO. 19

His Gly Glu Gly Thr Phe Thr Ser Asp Leu Ser Lys GIn Leu Glu Glu Ala Ala Val Arg Leu Phe Ile Glu Phe Leu Lys Asn-NH$_2$ [SEQ. ID. NO. 19]

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HIPLC (gradient 37% to 47% Solvent B in Solvent A over 30 minutes) of the lyophilized peptide gave product peptide having an observed retention time of 13.7 minutes. Electrospray Mass Spectrometry (M): calculated 3179.6; found 3179.0.

Example 19
Preparation of Peptide Having SEQ. ID. NO. 20

His Gly Glu Gly Thr Phe Thr Ser Asp Leu Ser Lys Gln Leu Glu Glu Glu Ala Ala Arg Leu Phe Ile Glu Phe Leu Lys Asn-NH$_2$ [SEQ. ID. NO. 20]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 14.0 minutes. Electrospray Mass Spectrometry (M): calculated 3209.6; found 3212.8.

Example 20
Preparation of Peptide Having SEQ. ID. NO. 21

His Gly Glu Gly Thr Phe Thr Ser Asp Leu Ser Lys Gln Leu Glu Glu Glu Ala Val Ala Leu Phe Ile Glu Phe Leu Lys Asn-NH$_2$ [SEQ. ID. NO. 21]

The above-identified amidated peptide was assembled on 4-(2'-4'-dimethoxyphenyl)-Fmoc aminomethyl phenoxy acetamide norleucine MBHA resin (Novabiochem, 0.55 mrnole/g) using Fmoc-protected amino acids (Applied Biosystems, Inc.), cleaved from the resin, deprotectcd and purified in a similar way to Example 4. Used in analysis were Solvent A (0.1°% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.3 minutes. Electrospray Mass Spectrometry (M): calculated 3152.5; found 3153.5.

Example 21
Preparation of Peptide Having SEQ. ID. NO. 22

His Gly Glu Gly Thr Phe Thr Ser Asp Leu Ser Lys Gln Leu Glu Glu Glu Ala Val Arg Ala Phe Ile Glu Phe Leu Lys Asn-NH$_2$ [SEQ. ID. NO. 22]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 12.1 minutes. Electrospray Mass Spectrometry (M): calculated 3195.5; found 3197.7.

Example 22
Preparation of Peptide Having SEQ. ID. NO. 23

His Gly Glu Gly Thr Phe Thr Ser Asp Leu Ser Lys Gln Leu Glu Glu Glu Ala Val Arg Leu Phe Ile Ala Phe Leu Lys Asn-NH$_2$ [SEQ. ID. NO. 23]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems. Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 10.9 minutes. Electrospray Mass Spectrometry (M): calculated 3179.6; found 3180.5.

Example 23
Preparation of Peptide Having SEQ. ID. NO. 24

His Gly Glu Gly Thr Phe Thr Ser Asp Leu Ser Lys Gln Leu Glu Glu Glu Ala Val Arg Leu Phe Ile Glu Ala Leu Lys Asn-NH$_2$ [SEQ. ID. NO. 24]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 17.5 minutes. Electrospray Mass Spectrometry (M): calculated 3161.5; found 3163.0.

Example 24
Preparation of Peptide Having SEQ. ID. NO. 25

His Gly Glu Gly Thr Phe Thr Ser Asp Leu Ser Lys Gln Leu Glu Glu Glu Ala Val Arg Leu Phe Ile Glu Phe Ala Lys Asn-NH$_2$ [SEQ. ID. NO. 25]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 32% to 42% Solvent B in Solvent A over 30 minutes) of the lyophilized peptide gave product peptide having an observed retention time of 19.5 minutes. Electrospray Mass Spectrometry (M): calculated 3195.5; found 3199.

Example 25
Preparation of Peptide Having SEQ. ID. NO. 26

His Gly Glu Gly Thr Phe Thr Ser Asp Leu Ser Lys Gln Leu Glu Glu Glu Ala Val Arg Leu Phe Ile Glu Phe Leu Ala Asn-NH$_2$ [SEQ. ID. NO. 26]

The above-identified amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 38% to 48% Solvent B in Solvent A over 30 minutes) of the lyophilized peptide gave product peptide having an observed retention time of 14.5 minutes. Electrospray Mass Spectrometry (M): calculated 3180.5; found 3183.7.

Example 26
Preparation of Peptide Having SEQ. ID. NO. 27

His Gly Glu Gly Thr Phe Thr Ser Asp Leu Ser Lys Gln Leu Glu Glu Glu Ala Val Arg Leu Phe Ile Glu Phe Leu Lys Ala-NH$_2$ [SEQ. ID. NO. 27]

The above-identified amidated peptide was assembled on 4-(2'-4'-dimethoxyphenyl)-Fmoc aminomethyl phenoxy acetamide norleucine MBHA resin (Novabiochem, 0.55 mmolc/g) using Fmoc-protected amino acids (Applied Biosystems, Inc.), cleaved from the resin, deprotected and purified in a similar way to Example 4. Used in analysis were Solvent A (0.1% TFA in water) and Solvent B (0.1% TFA in ACN). Analytical RP-HPLC (gradient 34% to 44% Solvent B in Solvent A over 30 minutes) of the lyophilized peptide gave product peptide having an observed retention time of 22.8 minutes. Electrospray Mass Spectrometry (M): calculated 3194.6; found 3197.6.

Example 27
Preparation of Peptide Having SEQ. ID. NO. 28
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-NH$_2$ [SEQ. ID. NO. 28]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4099.6.

Example 28
Preparation of Peptide Having SEQ. ID. NO. 29
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-NH$_2$ [SEQ. ID. NO. 29]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4042.5.

Example 29
Preparation of Peptide Having SEQ. ID. NO. 30
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-NH$_2$ [SEQ. ID. NO. 30]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems. Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4002.4.

Example 30
Preparation of Peptide Having SEQ. ID. NO. 31
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro-NH$_2$ [SEQ. ID. NO. 31]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3945.4.

Example 31
Preparation of Peptide Having SEQ. ID. NO. 32
His Gly Glu Gly Thr Phe Thr Ser Asp Leu Ser Lys Gln Met Glu Glu Glu Ala Val
Arg Leu Phe Ile Glu Trp Leu Lys Asn Gly Gly Pro Ser Ser Gly Ala Pro-NH$_2$ [SEQ. ID. NO. 32]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3905.3.

Example 32
Preparation of Peptide Having SEQ. ID. NO. 33
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro-NH$_2$ [SEQ. ID. NO. 33]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3848.2.

Example 33
Preparation of Peptide Having SEQ. ID. NO. 34
His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ. ID. NO. 34]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3808.2.

Example 34

Preparation of Peptide Having SEQ. ID. NO. 35

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-NH$_2$ [SEQ. ID. NO. 35]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.1.

Example 35

Preparation of Peptide Having SEQ. ID. NO. 36

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly-NH$_2$ [SEQ. ID. NO. 36]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3737.1.

Example 36

Preparation of Peptide Having SEQ. ID. NO. 37

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly-NH$_2$ [SEQ. ID. NO. 37]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1.

Example 37

Preparation of Peptide Having SEQ. ID. NO. 38

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser-NH$_2$ [SEQ. ID. NO. 38]

The above-identified amidated peptide is assembled on 4-(2'-4'-dimethoxyphenyl)-Fmoc aminomethyl phenoxy acetamide norleucine MBHA resin (Novabiochem 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3680.1.

Example 38

Preparation of Peptide Having SEQ. ID. NO. 39

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser-NH$_2$ [SEQ. ID. NO. 39]

The above-identified amidated peptide is assembled on 4-(2'-4'-dimethoxyphenyl)-Fmoc arninomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3623.0.

Example 39

Preparation of Peptide Having SEQ. ID. NO. 40

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser-NH$_2$ [SEQ. ID. NO. 40]

The above-identified amidated peptide is assembled on 4-(2'-4'-dimethoxyphenyl)-Fmoc aminomethyl phenoxy acetamide norleucine MBHA resin (Novabiochem 0.55 mmole/g) using Fmoc-protected amino acids (Applied Biosystems. Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3593.0.

Example 40

Preparation of Peptide Having SEQ. ID. NO. 41

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser-NH$_2$ [SEQ. ID. NO. 41]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3535.9.

Example 41
Preparation of Peptide Having SEQ. ID. NO. 42

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro-NH$_2$ [SEQ. ID. NO. 42]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems. Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3505.9.

Example 42
Preparation of Peptide Having SEQ. ID. NO. 43

His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro-NH$_2$ [SEQ. ID. NO. 43]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3448.8.

Example 43
Preparation of Peptide Having SEQ. ID. NO. 44

His Gly Glu Gly Thr Phe Thr Ser Asp Leu Ser Lys Gln Leu Glu Glu Glu Ala Val Arg Leu Phe Ile Glu Phe Leu Lys Asn Gly Gly-NH$_2$ [SEQ. ID. NO. 44]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.7.

Example 44
Preparation of Peptide Having SEQ. ID. NO. 45

His Gly Glu Gly Thr Phe Thr Ser Asp Leu Ser Lys Gln Met Glu Glu Glu Ala Val Arg Leu Phe Ile Glu Trp Leu Lys Asn Gly-NH$_2$ [SEQ. ID. NO. 45]

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3351.8.

Example 45
Preparation of Peptide Having SEQ. ID. NO. 46

His Gly Glu Gly Thr Phe Thr Ser Asp Leu Ser Lys Gln Leu Glu Glu Glu Ala Val Arg Leu Phe Ile Glu Phe Leu Lys Asn Gly-NH$_2$ [SEQ. ID. NO. 46]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

Example 46
Preparation of Peptide Having SEQ. ID. NO. 47

His Gly Glu Gly Thr Phe Thr Ser Asp Leu Ser Lys Gln Met Glu Glu Glu Ala Val Arg Leu Phe Ile Glu Trp Leu Lys Asn Gly Gly tPro Ser Ser Gly Ala tPro tPro tPro-NH$_2$ [SEQ. ID. NO. 47]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4197.1.

Example 47
Preparation of Peptide Having SEQ. ID. NO. 48

His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala tPro tPro tPro-NH$_2$ [SEQ. ID. NO. 48]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4179.1.

Example 48
Preparation of Peptide Having SEQ. ID. NO. 49

His Gly Glu Gly Thr Phe Thr Ser Asp Leu Ser Lys Gln Met Glu Glu Glu Ala Val Arg Leu Phe Ile Glu Trp Leu Lys Asn Gly Gly NMeala Ser Ser Gly Ala Pro Pro-NH$_2$ [SEQ. ID. NO. 49]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3948.3.

Example 49
Preparation of Peptide having SEQ. ID. NO. 50

His Gly Glu Gly Thr Phe Thr Ser Asp Leu Ser Lys Gln Met Glu Glu Glu Ala Val Arg Leu Phe Ile Glu Trp Leu Lys Asn Gly Gly NMeala Ser Ser Gly Ala NMeala Nmeala-NH$_2$ SEQ. ID. NO. 50

The above-identified amidated peptide is assembled on 4-(2'-4'-dimethoxyphenyl)-Fmoc aminomethyl phenoxy acetamide norleucine MBHA resin Novabiochem, 0.55 mmole/g) using Fmoc-protected amino acids (Applied Biosystems, Inc.), cleaved from the resin, deprotected and purified in a similar way to Example 4. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3840.1.

Example 50
Preparation of Peptide Having SEQ. ID. NO. 51

His Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro hPro-NH$_2$ [SEQ. ID. NO. 51]

The above-identified amidated peptide is assembled on 4-(2'-4'-dimethoxyphenyt)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4050.1.

Example 51
Preparation of Peptide Having SEQ. ID. NO. 52

His Gly Glu Gly Thr Phe Thr Ser Asp Leu Ser Lys Gln Met Glu Glu Glu Ala Val Arg Leu Phe Ile Glu Trp Leu Lys Asn Gly Gly hPro Ser Ser Gly Ala hPro-NH$_2$ [SEQ. ID. NO. 52]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3937.1.

Example 52
Preparation of Peptide Having SEQ. ID. NO. 53

Arg Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ [SEQ. ID. NO. 53]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3827.2.

Example 53
Preparation of Peptide Having SEQ. ID. NO. 54

His Gly Asp Gly Thr Phe Thr Ser Asp Leu Ser Lys Gln Met Glu Glu Glu Ala Val Arg Leu Phe Ile Glu Trp Leu Lys Asn Gly Gly-NH$_2$ [SEQ. ID. NO. 54]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3394.8.

Example 54
Preparation of Peptide Having SEQ. ID. NO. 55

His Gly Glu Gly Thr Naphthylala Thr Ser Asp Leu Ser Lys Gln Leu Glu Glu Glu Ala Val Arg Leu Phe Ile Glu Phe Leu Lys Asn-NH$_2$ [SEQ. ID. NO. 55]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

Example 55
Preparation of Peptide Having SEQ. ID. NO. 56

His Gly Glu Gly Thr Phe Ser Ser Asp Leu Ser Lys Gln Met Glu Glu Glu Ala Val Arg Leu Phe Ile Glu Trp Leu Lys Asn-NH$_2$ [SEQ. ID. NO. 56]

The above-identified amidated peptide is assembled on 4-(2'-4'-dimethoxyphenyl)-Fmoc arninomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3280.7.

Example 56
Preparation of Peptide Having SEQ. ID. NO. 57

His Gly Glu Gly Thr Phe Ser Thr Asp Leu Ser Lys Gln Met Glu Glu Glu Ala Val Arg Leu Phe Ile Glu Trp Leu Lys Asn-NH$_2$ [SEQ. ID. NO. 57]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3294.7.

Example 57
Preparation of Peptide Having SEQ. ID. NO. 58

His Gly Glu Gly Thr Phe Thr Ser Glu Leu Ser Lys Gln Met Ala Glu Glu Ala Val Arg Leu Phe Ile Glu Trp Leu Lys Asn-NH$_2$ [SEQ. ID. NO. 58]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7.

Example 58
Preparation of Peptide Having SEQ. ID. NO. 59

His Gly Glu Gly Thr Phe Thr Ser Asp pentylgly Ser Lys Gln Leu Glu Glu Glu Ala Val Arg Leu Phe Ile Glu Phe Leu Lys Asn-NH$_2$ [SEQ. ID. NO. 59]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3253.5.

Example 59
Preparation of Peptide Having SEQ. ID. NO. 60

His Gly Glu Gly Thr Phe Thr Ser Asp Leu Ser Lys Gln Leu Glu Glu Glu Ala Val Arg Leu Naphthylala Ile Glu Phe Leu Lys Asn-NH$_2$ [SEQ. ID. NO. 60]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3289.5.

Example 60
Preparation of Peptide Having SEQ. ID. NO. 61

His Gly Glu Gly Thr Phe Thr Ser Asp Leu Ser Lys Gln Met Glu Glu Glu Ala Val Arg Leu Phe tButylgly Glu Trp Leu Lys Asn-NH$_2$ [SEQ. ID. NO. 61]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3183.4.

Example 61
Preparation of Peptide Having SEQ. ID. NO. 62

His Gly Glu Glu Thr Phe Thr Ser Asp Leu Ser Lys Gln Leu Glu Glu Glu Ala Val Arg Leu
Phe Ile Asp Phe Leu Lys Asn-NH$_2$ [SEQ. ID. NO. 62]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3237.6.

Example 62
Preparation of Peptide having SEQ. ID. NO. 63

His Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser-NH$_2$ [SEQ. ID. NO. 63]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3637.9.

Example 63
Preparation of Peptide Having SEQ. ID. NO. 64

His Gly Glu Gly Thr Phe Thr Ser Asp Ala Ser Lys Gln Met Glu Glu Glu Ala Val Arg Leu Phe Ile Glu Trp Leu Lys Asn Gly-NH$_2$ [SEQ. ID. NO. 64]

The above-identified amidated peptide is assembled on 4-(2'-4'-dimethoxyphenyl)-Fmoc arninomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3309.7.

Example 64
Preparation of Peptide Having SEQ. ID. NO. 65

His Gly Glu Gly Thr Phe Thr Ser Asp Ala Ser Lys Gln Met Glu Glu Glu Ala Val Arg Leu Phe Ile Glu Trp Leu Lys Asn Gly Gly hPro Ser Ser Gly Ala hPro hPro-NH$_2$ [SEQ. ID. NO. 65]

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3711.1.

Example 65
Preparation of C-terminal Carboxylic Acid Peptides Corresponding to the Above C-terminal Amide Sequences for SEQ. ID. NOS. 5–27, 34–41, 44–46 and 53–64

Peptides having the sequences of SEQ. ID. NOS. 5–27, 34–41, 44–46 and 53–64 are assembled on the so called Wang resin (p-alkoxybenzylalcohol resin (Bachem, 0.54 mmole/g)) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

Example 66
Preparation of C-terminal Carboxylic Acid Peptides Corresponding to the Above C-terminal Amide Sequences for SEQ. ID. NOS. 28–33, 42, 43, 47–52 and 65

Peptides having the sequence of SEQ. ID. NOS. 28–33, 42, 43, 47–52 and 65 are assembled on the 2-chlorotritylchloride resin (200–400 mesh), 2% DVB (Novabiochem, 0.4–1.0 mmole/g)) using Fmoc-protected amino acids (Applied Biosystems. Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

---

We claim:

1. A method for increasing urine flow in an individual in need thereof comprising administering an amount of an exendin or an exendin agonist effective to increase urine flow.

2. The method of claim 1, wherein said increase in urine flow is accompanied by an increase in sodium excretion in said individual.

3. The method of claim 1, wherein said increase in urine flow does not increase urinary potassium concentration in said individual.

4. A method of decreasing the concentration of potassium in the urine of an individual in need thereof comprising administering to said individual an amount of an exendin or an exendin agonist effective to decrease the concentration of potassium in the urine.

5. A method of alleviating a condition or disorder associated with toxic hypervolemia in an individual, comprising administering to said individual a therapeutically effective amount of an exendin or an exendin agonist.

6. The method of claim 5, wherein the condition or disorder is rental failure.

7. The method of claim 5, wherein said condition or disorder is hypertension.

8. A method of inducing rapid diuresis in an individual in need of diuresis comprising administering to said individual an amount of an exendin or an exendin agonist effective to induce diuresis.

9. A method of preparing an individual for a surgical procedure comprising administering to said individual a therapeutically effective amount of an exendin or an exendin agonist.

10. The method of claim 9, wherein said surgical procedure is selected from the group consisting of ocular surgical procedures and neurosurgical procedures.

11. The method of claim 9, wherein said exendin or exendin agonist is administered to said individual before said surgical procedure.

12. A method of increasing renal plasma flow and glomerular filtration rate in an individual in need thereof comprising administering to said individual an amount of an exendin or an exendin agonist effective to increase renal plasma flow and glomerular filtration rate.

13. A method of treating pre-eclampsia or eclampsia of pregnancy in an individual having pre-eclampsia or eclampsia, comprising administering to said individual a therapeutically effective amount of an exendin or an exendin agonist.

14. The method according to any of claims 1, 4, 5, 8, 9, 12, or 13, wherein said exendin is exendin-3 [SEQ ID NO. 1].

15. The method according to any of claims 1, 4, 5, 8, 9, 12, or 13, wherein said exendin is exendin-4 [SEQ ID NO. 2].

16. The method according to any of claims 1, 4, 5, 8, 9, 12 or 13, wherein said exendin agonist is a peptide compound of the formula [SEQ. ID. NO. 4]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gin;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
  —$NH_2$,
  Gly-$Z_2$,
  Gly Gly-$Z_2$,
  Gly Gly $Xaa_{31}$-$Z_2$,
  Gly Gly $Xaa_{31}$ Ser-$Z_2$,
  Gly Gly $Xaa_{31}$ Ser Ser-$Z_2$, Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$,
Gly Gly $Xaa_{31}$ Ser Ser Gly Ala $Xaa_{36}$ $Xaa_{37}$ $Xaa_{38}$-$Z_2$, or
Gly Gly Xaa31 Ser Ser Gly Ala $Xaa_{36}$ $Xaa_{37}$ $Xaa_{38}$ $Xaa_{39}$-$Z_2$; wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; $Xaa_{39}$ is Ser, Thr or Tyr; and $Z_2$ is —OH or —$NH_2$; and pharmaceutically acceptable salts thereof;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and provided also that the compound is not exendin-3 [SEQ ID NO. 1] or exendin-4 [SEQ ID NO. 2].

17. The method according to any of claims 1, 4, 5, 8, 9, 12, or 13, wherein said exendin or exendin agonist is administered peripherally.

18. The method according to claim 17, wherein said exendin or exendin agonist is administered subcutaneously.

19. The method of claim 17, wherein said peripheral administration is selected from the group consisting of buccal, nasal, pulmonary, oral, intravenous, intraocular, rectal, and transdermal administration.

20. The method of claim 5, wherein the condition or disorder is congestive heart failure.

21. The method of claim 5, wherein the condition or disorder is nephrotic syndrome.

22. The method of claim 5, wherein the condition or disorder is pulmonary edema.

23. The method of claim 5, wherein the condition or disorder is cirrhosis.

24. A method for increasing cardiac contractility in an individual in need thereof comprising administering an amount of an exendin or an exendin agonist effective to increase cardiac contractility.

25. A method for treating a condition or disorder that can be alleviated by increasing cardiac contractility in an individual having said condition or disorder comprising administering an amount of an exendin or an exendin agonist effective to increase cardiac contractility.

26. The method according to claim 25 wherein said condition or disorder is congestive heart failure.

27. The method according to claim 24 or claim 25 wherein said exendin is exendin-3 [SEQ ID NO. 1].

28. The method according to claim 24 or claim 25 wherein said exendin is exendin-4 [SEQ ID NO. 2].

29. The method according to claim 24 or 25 wherein said exendin agonist is a peptide compound of the formula [SEQ. ID. NO. 4]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg or Tyr;
$Xaa_2$ is Ser, Gly, Ala or Thr;
$Xaa_3$ is Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
—$NH_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$,
Gly Gly $Xaa_{31}$ Ser Ser Gly Ala $Xaa_{36}$ $Xaa_{37}$ $Xaa_{38}$-$Z_2$, or
Gly Gly $Xaa_{31}$ Ser Ser Gly Ala $Xaa_{36}$ $Xaa_{37}$ $Xaa_{38}$ $Xaa_{39}$-$Z_2$;

wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; $Xaa_{39}$ is Ser, Thr or Tyr; and $Z_2$ is —OH or —$NH_2$; and pharmaceutically acceptable salts thereof;

provided that no more than three of $Xaa_3$, $Xaa_5$, $Xaa_6$, $Xaa_8$, $Xaa_{10}$. $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and provided also that the compound is not exendin-3 [SEQ. ID. NO. 1] or exendin-4 [SEQ ID NO. 2].

30. The method according to claim 24 or claim 25 wherein said exendin or exendin agonist is administered peripherally.

31. The method according to claim 30 wherein said peripheral administration is selected from the group consisting of buccal, nasal, pulmonary, oral, intraocular, rectal, and transdermal administration.

32. The method according to claim 24 or claim 25 wherein said exendin or exendin agonist is administered intravenously.

33. The method according to claim 25 wherein the condition or disorder is pulmonary edema.

34. The method according to claim 25 wherein the condition or disorder is systemic edema.

35. The method according to claim 25 wherein the condition or disorder is renal failure.

36. A method of increasing urine flow in an individual in need thereof comprising administering a compound selected from the group consisting of an exendin, an exendin agonist, a GLP-1, and a GLP-1 agonist in an amount effective to increase urine flow.

37. A method of decreasing the concentration of potassium in the urine of an individual in need thereof comprising administering a compound selected from the group consisting of an exendin, an exendin agonist, a GLP-1, and a GLP-1 agonist in an amount effective to decrease the concentration of potassium in the urine.

38. A method of inducing diuresis in an individual in need thereof comprising administering a compound selected from the group consisting of an exendin, an exendin agonist, a GLP-1, and a GLP-1 agonist in an amount effective to induce diuresis.

39. A method of increasing cardiac contractility in an individual in need thereof comprising administering a compound selected from the group consisting of an exendin, an exendin agonist, a GLP-1, and a GLP-1 agonist in an amount effective to increase cardiac contractility.

40. A method of alleviating a condition or disorder associated with toxic hypervolemia in an individual having such a condition, comprising administering a therapeutically effective amount of a compound selected from the group consisting of an exendin, an exendin agonist, a GLP-1, and a GLP-1 agonist.

41. A method of treating pre-eclampsia or eclampsia of pregnancy in a subject in need thereof, comprising administering a therapeutically effective amount of a compound selected from the group consisting of an exendin, an exendin agonist, a GLP-1, and a GLP-1 agonist.

42. A method of treating a condition or disorder that can be alleviated by increasing cardiac contractility in a subject having such a condition, comprising administering a therapeutically effective amount of a compound selected from the group consisting of an exendin, an exendin agonist, a GLP-1, and a GLP-1 agonist.

* * * * *

UNITED STATES PATENT AND TRADEMARK OFFICE
CERTIFICATE OF CORRECTION

PATENT NO.    : 6,703,359 B1
DATED         : March 9, 2004
INVENTOR(S)   : Andrew A. Young et al.

It is certified that error appears in the above-identified patent and that said Letters Patent is hereby corrected as shown below:

Title page,
Item [54], Title, please amend the title to read -- [54] INOTROPIC AND DIURETIC EFFECTS OF EXENDIN --.

Column 1,
Line 2, delete "AND GLP-1".
Line 48, change "commonly, just GLP-1," to -- commonly, just "GLP-1," --;
Lines 50 and 51, change "-cells" to -- β-cells --.

Column 2,
Line 1, change "-cells" to -- β-cells --.

Line 27, change "TC1" to -- βTC1 --.

Column 3,
Line 2, from the bottom, change "Gilman s" to -- Gilman's --.

Column 4,
Line 2, change "(Harrison s" to -- Harrison's --;
Line 13, change "fumction" to -- function --;
Line 15, change "in" to -- to --;
Line 20, change "t" to -- $t_{½}$ --;
Line 26, change "arrhhthmia" to -- arrhythmia --;
Line 39, after "after" insert -- ~ --.

Column 5,
Line 37, change "conunon" to -- common --.

Column 7,
Line 21, change "1 g-30 g" to -- 1μg - 30μg --;
Line 23, change "g to" to -- μg to -- and change "300 g" to -- 300 μg --;
Line 25, change "30 g" to -- 30μg --.

Column 8,
Line 24, after "of" insert -- a --;
Line 46, change "1 g- 30 g" to -- 1μg - 30μg --;
Lines 48 and 50, change "30 g" to -- 30 μg --.
Line 49, change "300 g" to -- 300 μg --.

UNITED STATES PATENT AND TRADEMARK OFFICE
CERTIFICATE OF CORRECTION

PATENT NO. : 6,703,359 B1
DATED : March 9, 2004
INVENTOR(S) : Andrew A. Young et al.

It is certified that error appears in the above-identified patent and that said Letters Patent is hereby corrected as shown below:

Column 9,
Line 28, change "pulmonaryv," to -- pulmonary, --.

Column 13,
Line 41, change "—CH(R)—, wherein R" to -- —CH(R')—, where R' --.

Column 75,
Line 22, change "rental" to -- renal --.

Column 78,
Lines 61 through 67, delete in their entirety.

Columns 79 and 80,
Delete in their entirety.

Signed and Sealed this

Thirty-first Day of August, 2004

JON W. DUDAS
*Director of the United States Patent and Trademark Office*